US012758718B2

(12) United States Patent
Kachler et al.

(10) Patent No.: US 12,758,718 B2
(45) Date of Patent: Oct. 13, 2026

(54) SYSTEM AND METHOD FOR NEEDLE HIDING IN INJECTORS

(71) Applicant: PFIZER, INC., New York, NY (US)

(72) Inventors: Ilan Kachler, Nahariya (IL); Idan Naaman, Upper Galilee (IL); Amotz Porat, West Galilee (IL); Tom Shefer, West Galilee (IL)

(73) Assignee: PFIZER, INC., New York, NY (US)

( * ) Notice: Subject to any disclaimer, the term of this patent is extended or adjusted under 35 U.S.C. 154(b) by 699 days.

(21) Appl. No.: 18/036,760

(22) PCT Filed: Nov. 12, 2021

(86) PCT No.: PCT/IB2021/060507
§ 371 (c)(1),
(2) Date: May 12, 2023

(87) PCT Pub. No.: WO2022/101844
PCT Pub. Date: May 19, 2022

(65) Prior Publication Data
US 2024/0017019 A1 Jan. 18, 2024

Related U.S. Application Data
(60) Provisional application No. 63/114,008, filed on Nov. 16, 2020.

(51) Int. Cl.
*A61M 5/32* (2006.01)
(52) U.S. Cl.
CPC .............................. *A61M 5/3257* (2013.01)

(58) Field of Classification Search
CPC .............. A61M 5/3257; A61M 5/3271; A61M 5/31591; A61M 2005/2073;
(Continued)

(56) References Cited

U.S. PATENT DOCUMENTS 3,702,608 A 11/1972 Tibbs
3,880,163 A 4/1975 Ritterskamp
(Continued)

FOREIGN PATENT DOCUMENTS

CA 3026818 A1 12/2017
EP 855922 A1 8/1998
(Continued)

OTHER PUBLICATIONS

International Search Report and Written Opinion of the International Searching Authority issued in International Application No. PCT/IB2021/060507, 9 pages, dated Nov. 12, 2021.

*Primary Examiner* — Chelsea E Stinson
*Assistant Examiner* — Eric A Lange
(74) *Attorney, Agent, or Firm* — DLA Piper LLP US

(57) ABSTRACT

An injector, comprising a housing arranged along a longitudinal axis and configured to receive a medicament cartridge; an injection drive mechanism for driving a piston, the piston forming part of the medicament cartridge, the injection drive mechanism injecting a medicament when the piston is forwardly displaced; and a needle hiding element, which is slidably attached to the housing and positionable in at least one of an extended orientation and a retracted orientation, wherein in the extended orientation the needle hiding element protrudes forwardly from the housing and in the retracted orientation, the needle hiding element is locked relative to the housing.

17 Claims, 18 Drawing Sheets

(58) Field of Classification Search
CPC ........... A61M 2005/2414; A61M 2005/31588; A61M 5/20; A61M 5/3245; A61M 2005/3247; A61M 2005/3246; A61M 5/3243
See application file for complete search history.

(56) References Cited

U.S. PATENT DOCUMENTS 4,333,459 A 6/1982 Becker
4,923,447 A * 5/1990 Morgan .............. A61M 5/3271 604/263
5,026,343 A 6/1991 Holzer
5,106,379 A * 4/1992 Leap .................. A61M 5/3271 604/263
5,201,708 A * 4/1993 Martin ................ A61M 5/3271 604/110
5,505,697 A 4/1996 McKinnon et al.
5,569,190 A 10/1996 D'Antonio
5,582,598 A 12/1996 Chanoch
5,695,475 A 12/1997 Best et al.
5,868,710 A 2/1999 Battiato et al.
6,056,716 A 5/2000 D'Antonio
6,146,109 A 11/2000 Davis
6,171,276 B1 1/2001 Lippe
6,277,098 B1 8/2001 Klitmose et al.
6,362,591 B1 3/2002 Moberg
6,482,185 B1 11/2002 Hartmann
6,547,755 B1 4/2003 Lippe et al.
6,555,986 B2 4/2003 Moberg et al.
6,585,698 B1 7/2003 Packman et al.
6,589,210 B1 7/2003 Rolfe
6,595,962 B1 7/2003 Perthu
6,599,272 B1 7/2003 Hjertman et al.
6,685,678 B2 2/2004 Evans
6,743,202 B2 6/2004 Hirschman et al.
6,854,620 B2 2/2005 Ramey
6,929,619 B2 8/2005 Fago et al.
6,942,646 B2 9/2005 Langley et al.
6,997,906 B2 2/2006 Langley et al.
7,029,459 B2 4/2006 Reilly
7,052,484 B2 5/2006 Veasey et al.
7,074,211 B1 7/2006 Heiniger et al.
7,194,749 B2 3/2007 Hatazawa
7,322,955 B2 1/2008 Azizi et al.
7,397,730 B2 7/2008 Skyggbjerg et al.
7,416,540 B2 8/2008 Edwards
7,462,166 B2 12/2008 Kowan et al.
7,465,290 B2 12/2008 Reilly
7,597,682 B2 10/2009 Moberg
7,621,893 B2 11/2009 Moberg et al.
7,648,482 B2 1/2010 Edwards et al.
7,648,483 B2 1/2010 Edwards et al.
7,686,789 B2 3/2010 Nemoto et al.
7,704,231 B2 4/2010 Pongpairochana et al.
7,740,612 B2 6/2010 Hochman
7,749,194 B2 7/2010 Edwards et al.
7,766,873 B2 8/2010 Moberg et al.
7,794,429 B2 9/2010 Niehoff
7,828,776 B2 11/2010 Nemoto et al.
7,833,196 B2 11/2010 Estes et al.
7,854,726 B2 12/2010 Fago et al.
7,859,473 B2 12/2010 Gibson
7,871,393 B2 1/2011 Monroe
7,898,416 B2 3/2011 Fago et al.
7,922,699 B2 4/2011 Baba et al.
7,967,784 B2 6/2011 Pongpairochana et al.
7,975,922 B2 7/2011 Fago et al.
7,993,300 B2 8/2011 Nyholm et al.
8,035,517 B2 10/2011 Gibson
8,044,778 B2 10/2011 Monroe
8,128,603 B2 3/2012 Langley et al.
8,141,417 B2 3/2012 Gibson et al.
8,149,111 B2 4/2012 Monroe
8,177,747 B2 5/2012 Pinedjian
8,177,749 B2 5/2012 Slate et al.
8,206,360 B2 6/2012 Edwards et al.
8,211,062 B2 7/2012 Estes et al.
8,226,610 B2 7/2012 Edwards et al.
8,231,573 B2 7/2012 Edwards et al.
8,287,500 B2 10/2012 Baba et al.
8,313,466 B2 11/2012 Edwards et al.
8,333,752 B2 12/2012 Veit et al.
8,361,026 B2 1/2013 Edwards et al.
8,366,680 B2 2/2013 Raab
8,376,985 B2 2/2013 Pongpairochana et al.
8,376,993 B2 2/2013 Cox et al.
8,381,029 B2 2/2013 Koshiyama
8,500,692 B2 8/2013 Yodfat et al.
8,544,645 B2 10/2013 Edwards et al.
8,632,511 B2 1/2014 Dos Santos et al.
8,641,669 B2 2/2014 Renz et al.
8,647,296 B2 2/2014 Moberg et al.
8,663,201 B2 3/2014 Hill et al.
8,690,827 B2 4/2014 Edwards et al.
8,715,224 B2 5/2014 Kamen et al.
8,784,378 B2 7/2014 Weinandy
8,827,962 B2 9/2014 Giambattista et al.
8,834,420 B2 9/2014 Estes et al.
8,858,508 B2 10/2014 Lavi et al.
8,870,827 B2 10/2014 Young et al.
8,920,374 B2 12/2014 Bokelman et al.
8,926,594 B2 1/2015 Edwards et al.
8,932,254 B2 1/2015 Eaton
8,936,565 B2 1/2015 Chawla
8,968,256 B2 3/2015 Raab
8,974,413 B2 3/2015 Baba et al.
9,011,371 B2 4/2015 Moberg et al.
9,149,579 B2 10/2015 Edwards et al.
9,192,728 B2 11/2015 Gilmore et al.
9,238,108 B2 1/2016 Edwards et al.
9,278,177 B2 3/2016 Edwards et al.
9,283,325 B2 3/2016 Karlsson
9,297,370 B2 3/2016 Brueggemann et al.
9,345,841 B2 5/2016 Plumptre et al.
9,381,300 B2 7/2016 Smith et al.
9,421,334 B2 8/2016 Quinn et al.
9,457,154 B2 10/2016 Moller et al.
9,474,857 B2 10/2016 Riley et al.
9,492,618 B2 11/2016 Day
9,504,793 B2 11/2016 Eggert et al.
9,514,131 B1 12/2016 Bochenko et al.
9,572,932 B2 2/2017 Eggert et al.
9,956,343 B2 5/2018 Murakami et al.
10,463,800 B2 11/2019 Baba et al.
2001/0005781 A1 6/2001 Bergens et al.
2001/0056263 A1* 12/2001 Alchas .................... A61M 5/32 604/196
2003/0114836 A1 6/2003 Estes et al.
2003/0120209 A1 6/2003 Jensen et al.
2004/0024364 A1 2/2004 Langley et al.
2004/0024631 A1 2/2004 Fago et al.
2004/0054318 A1 3/2004 Langley et al.
2004/0054319 A1 3/2004 Langley et al.
2004/0054328 A1 3/2004 Langley et al.
2004/0236284 A1* 11/2004 Hoste .................... A61M 5/326 604/198
2005/0020979 A1 1/2005 Westbye et al.
2005/0055242 A1 3/2005 Bello et al.
2005/0182323 A1 8/2005 Grispo et al.
2005/0197650 A1 9/2005 Sugimoto et al.
2005/0254348 A1 11/2005 Niemiec et al.
2007/0167920 A1 7/2007 Hommann
2007/0197968 A1 8/2007 Pongpairochana
2007/0197974 A1 8/2007 Gibson
2008/0015512 A1 1/2008 D'Antonio et al.
2008/0031259 A1 2/2008 Zampiello
2008/0059133 A1 3/2008 Edwards et al.
2008/0125724 A1 5/2008 Monroe
2009/0076458 A1 3/2009 Neilsen et al.
2010/0211005 A1 8/2010 Edwards et al.
2010/0318035 A1 12/2010 Edwards et al.
2011/0004165 A1 1/2011 Iilo et al.
2011/0009821 A1 1/2011 Jespersen et al.
2011/0033832 A1 2/2011 Baba et al.

(56) References Cited

U.S. PATENT DOCUMENTS

| | | | |
|---|---|---|---|
| 2011/0062703 A1 | 3/2011 | Lopez et al. | |
| 2011/0118694 A1 | 5/2011 | Yodfat et al. | |
| 2011/0166521 A1 | 7/2011 | Marshall et al. | |
| 2011/0178473 A1* | 7/2011 | Richards | A61M 5/3257 604/198 |
| 2011/0201998 A1 | 8/2011 | Pongpairochana et al. | |
| 2011/0224614 A1 | 9/2011 | Moberg et al. | |
| 2011/0224616 A1 | 9/2011 | Slate et al. | |
| 2011/0270214 A1 | 11/2011 | Joergensen et al. | |
| 2011/0279271 A1 | 11/2011 | Monroe | |
| 2011/0284577 A1 | 11/2011 | Nemoto et al. | |
| 2011/0288481 A1 | 11/2011 | Mudd et al. | |
| 2011/0301534 A1 | 12/2011 | Renz et al. | |
| 2011/0301566 A1 | 12/2011 | Schaefer | |
| 2012/0022458 A1 | 1/2012 | Oh et al. | |
| 2012/0029349 A1 | 2/2012 | Bruce et al. | |
| 2012/0044070 A1 | 2/2012 | Putrino | |
| 2012/0056019 A1 | 3/2012 | Renz et al. | |
| 2012/0101439 A9 | 4/2012 | Slate et al. | |
| 2012/0101470 A1 | 4/2012 | Rasmussen et al. | |
| 2012/0107783 A1 | 5/2012 | Julian et al. | |
| 2012/0116311 A1 | 5/2012 | Brueggemann et al. | |
| 2012/0179016 A1 | 7/2012 | Iio et al. | |
| 2012/0203178 A1 | 8/2012 | Tverskoy | |
| 2012/0226226 A1 | 9/2012 | Edwards et al. | |
| 2012/0233834 A1 | 9/2012 | Szechinski et al. | |
| 2012/0265142 A1 | 10/2012 | Slate et al. | |
| 2012/0280815 A1 | 11/2012 | Edwards et al. | |
| 2012/0323176 A1 | 12/2012 | Watanabe et al. | |
| 2013/0046246 A1 | 2/2013 | Cross et al. | |
| 2013/0053692 A1 | 2/2013 | Barron et al. | |
| 2013/0067416 A1 | 3/2013 | Barron et al. | |
| 2013/0123685 A1 | 5/2013 | Jespersen et al. | |
| 2013/0138040 A1 | 5/2013 | Weinandy | |
| 2013/0146615 A1 | 6/2013 | Gaudet | |
| 2013/0172819 A1 | 7/2013 | Toshiaki et al. | |
| 2013/0184649 A1 | 7/2013 | Edwards et al. | |
| 2013/0190692 A1 | 7/2013 | Edwards et al. | |
| 2013/0261563 A1 | 10/2013 | Zachek et al. | |
| 2013/0274655 A1 | 10/2013 | Jennings et al. | |
| 2013/0289480 A1* | 10/2013 | Roberts | A61M 5/3204 604/110 |
| 2013/0317324 A1 | 11/2013 | Yodfat et al. | |
| 2014/0012229 A1 | 1/2014 | Bokelman et al. | |
| 2014/0039404 A1 | 2/2014 | Young et al. | |
| 2014/0039407 A1 | 2/2014 | Schoonmaker | |
| 2014/0114258 A1 | 4/2014 | Day | |
| 2014/0142499 A1 | 5/2014 | Moberg et al. | |
| 2014/0142544 A1 | 5/2014 | Atterbury et al. | |
| 2014/0148785 A1 | 5/2014 | Moberg et al. | |
| 2014/0155827 A1 | 6/2014 | Ostrander et al. | |
| 2014/0163339 A1 | 6/2014 | Goldstein et al. | |
| 2014/0188048 A1 | 7/2014 | Edwards et al. | |
| 2014/0228763 A1 | 8/2014 | Kondoh et al. | |
| 2014/0243749 A1 | 8/2014 | Edwards et al. | |
| 2014/0249412 A1 | 9/2014 | Yamamoto | |
| 2014/0257185 A1 | 9/2014 | Bechmann et al. | |
| 2014/0276414 A1 | 9/2014 | Baker et al. | |
| 2014/0296782 A1 | 10/2014 | Ulrich et al. | |
| 2014/0296824 A1 | 10/2014 | Edwards et al. | |
| 2014/0303560 A1 | 10/2014 | Yates et al. | |
| 2014/0309616 A1 | 10/2014 | Edwards et al. | |
| 2014/0323982 A1 | 10/2014 | Lumme et al. | |
| 2014/0330203 A1 | 11/2014 | Mcloughlin et al. | |
| 2014/0336587 A1 | 11/2014 | Mcloughlin et al. | |
| 2014/0350470 A1 | 11/2014 | Gyory et al. | |
| 2014/0358072 A1 | 12/2014 | Mcloughlin et al. | |
| 2014/0358084 A1 | 12/2014 | Mcloughlin et al. | |
| 2014/0358085 A1 | 12/2014 | Mcloughlin et al. | |
| 2014/0378911 A1 | 12/2014 | Dolk et al. | |
| 2014/0379874 A1 | 12/2014 | Starr et al. | |
| 2015/0011944 A1 | 1/2015 | Young et al. | |
| 2015/0011973 A1 | 1/2015 | Edwards et al. | |
| 2015/0025375 A1 | 1/2015 | Pollard et al. | |
| 2015/0025457 A1 | 1/2015 | Moberg et al. | |
| 2015/0045729 A1 | 2/2015 | Denzer et al. | |
| 2015/0051580 A1 | 2/2015 | Shain et al. | |
| 2015/0078536 A1 | 3/2015 | Denny et al. | |
| 2015/0105903 A1 | 4/2015 | Denny et al. | |
| 2015/0133855 A1 | 5/2015 | Smith et al. | |
| 2015/0157803 A1 | 6/2015 | Radmer et al. | |
| 2015/0165135 A1 | 6/2015 | Mcloughlin et al. | |
| 2015/0174326 A1 | 6/2015 | Bokelman et al. | |
| 2015/0174335 A1* | 6/2015 | Roervig | A61M 5/347 604/198 |
| 2015/0182691 A1 | 7/2015 | Mcloughlin et al. | |
| 2015/0202365 A1 | 7/2015 | Roervig et al. | |
| 2015/0202367 A1 | 7/2015 | Plaschkes et al. | |
| 2015/0202374 A1 | 7/2015 | Mcloughlin et al. | |
| 2015/0250954 A1 | 9/2015 | Keitzmann et al. | |
| 2015/0250956 A1 | 9/2015 | Ostrander et al. | |
| 2015/0251839 A1 | 9/2015 | Denny et al. | |
| 2015/0314073 A1 | 11/2015 | Shang et al. | |
| 2015/0328404 A1 | 11/2015 | Murakami et al. | |
| 2015/0343157 A1 | 12/2015 | Basile et al. | |
| 2015/0359967 A1 | 12/2015 | Steel et al. | |
| 2015/0359977 A1 | 12/2015 | Watanabe et al. | |
| 2016/0001005 A1 | 1/2016 | Bechmann et al. | |
| 2016/0015897 A1 | 1/2016 | Swanson et al. | |
| 2016/0082195 A1 | 3/2016 | Atterbury et al. | |
| 2016/0106927 A1 | 4/2016 | Moeller et al. | |
| 2016/0119753 A1 | 4/2016 | Ostrander et al. | |
| 2016/0120751 A1 | 5/2016 | Mounce et al. | |
| 2016/0121056 A1 | 5/2016 | Edwards et al. | |
| 2016/0166768 A1 | 6/2016 | Edwards et al. | |
| 2016/0175515 A1 | 6/2016 | Mccullough | |
| 2016/0175527 A1 | 6/2016 | Mccullough | |
| 2016/0193414 A1 | 7/2016 | Mcloughlin et al. | |
| 2016/0235916 A1 | 8/2016 | Edwards et al. | |
| 2016/0243318 A1 | 8/2016 | Despa et al. | |
| 2016/0256630 A1 | 9/2016 | Kramer et al. | |
| 2016/0271323 A1 | 9/2016 | Bruggemann et al. | |
| 2016/0331901 A1 | 11/2016 | Grubbe et al. | |
| 2016/0339178 A1 | 11/2016 | Baker et al. | |
| 2016/0354553 A1 | 12/2016 | Anderson et al. | |
| 2017/0043092 A1 | 2/2017 | Murakami et al. | |
| 2017/0143908 A1 | 5/2017 | Eggert et al. | |
| 2017/0266390 A1 | 9/2017 | Baba et al. | |
| 2017/0290996 A1 | 10/2017 | Davies et al. | |
| 2019/0381253 A1 | 12/2019 | Baba et al. | |
| 2020/0197609 A1 | 6/2020 | Pikan et al. | |
| 2023/0201460 A1 | 6/2023 | Pikan et al. | |

FOREIGN PATENT DOCUMENTS

| | | | |
|---|---|---|---|
| EP | 0921828 | A1 | 6/1999 |
| EP | 1001821 | A1 | 5/2000 |
| EP | 1087808 | A1 | 4/2001 |
| EP | 1240913 | A2 | 9/2002 |
| EP | 1349591 | A1 | 10/2003 |
| EP | 1349592 | A1 | 10/2003 |
| EP | 1349593 | A1 | 10/2003 |
| EP | 1349594 | A1 | 10/2003 |
| EP | 1349595 | A1 | 10/2003 |
| EP | 1349596 | A1 | 10/2003 |
| EP | 1353713 | A1 | 10/2003 |
| EP | 1461099 | A1 | 9/2004 |
| EP | 1467785 | A1 | 10/2004 |
| EP | 1551480 | A1 | 7/2005 |
| EP | 1715904 | A2 | 11/2006 |
| EP | 1723977 | A1 | 11/2006 |
| EP | 1880330 | A1 | 1/2008 |
| EP | 2083887 | A1 | 5/2008 |
| EP | 1932556 | A1 | 6/2008 |
| EP | 1998751 | A2 | 12/2008 |
| EP | 2051755 | A1 | 4/2009 |
| EP | 2125075 | A2 | 12/2009 |
| EP | 2298391 | A1 | 3/2011 |
| EP | 2319561 | A2 | 5/2011 |
| EP | 2319562 | A1 | 5/2011 |
| EP | 2319563 | A1 | 5/2011 |
| EP | 2355858 | A1 | 8/2011 |
| EP | 2359884 | A2 | 8/2011 |
| EP | 2361647 | A1 | 8/2011 |

(56) References Cited

FOREIGN PATENT DOCUMENTS

| | | | |
|---|---|---|---|
| EP | 2384207 | A1 | 11/2011 |
| EP | 2468338 | A1 | 6/2012 |
| EP | 2469437 | A1 | 6/2012 |
| EP | 2526986 | A1 | 11/2012 |
| EP | 2574357 | A1 | 4/2013 |
| EP | 2609949 | A1 | 7/2013 |
| EP | 2714135 | A2 | 4/2014 |
| EP | 2714141 | A1 | 4/2014 |
| EP | 2714146 | A1 | 4/2014 |
| EP | 2311510 | B1 | 5/2014 |
| EP | 2756858 | A1 | 7/2014 |
| EP | 2760506 | A1 | 8/2014 |
| EP | 2007450 | B1 | 12/2014 |
| EP | 2869871 | A1 | 5/2015 |
| EP | 2879735 | A1 | 6/2015 |
| EP | 2879736 | A1 | 6/2015 |
| EP | 2879737 | A1 | 6/2015 |
| EP | 2892590 | A1 | 7/2015 |
| EP | 2908888 | A1 | 8/2015 |
| EP | 2925272 | A1 | 10/2015 |
| EP | 2926328 | A1 | 10/2015 |
| EP | 2928526 | A1 | 10/2015 |
| EP | 2932993 | A1 | 10/2015 |
| EP | 2949356 | A1 | 12/2015 |
| EP | 2953667 | A1 | 12/2015 |
| EP | 2965772 | A1 | 1/2016 |
| EP | 2968760 | A1 | 1/2016 |
| EP | 2968769 | A2 | 1/2016 |
| EP | 2968773 | A1 | 1/2016 |
| EP | 2968775 | A2 | 1/2016 |
| EP | 3003430 | A1 | 4/2016 |
| EP | 3033127 | A2 | 6/2016 |
| EP | 3082912 | A1 | 10/2016 |
| EP | 3127569 | A1 | 2/2017 |
| EP | 3178505 | A1 | 6/2017 |
| EP | 2229201 | A1 | 9/2020 |
| GB | 2565978 | A | 2/2019 |
| GB | 2601424 | A | 6/2022 |
| GB | 2606087 | A | 10/2022 |
| JP | 2002272839 | A | 9/2002 |
| JP | 2004305361 | A | 11/2004 |
| JP | 2012081283 | A | 4/2012 |
| JP | 5717649 | A | 6/2012 |
| JP | 2014012214 | A | 1/2014 |
| JP | 2016025934 | A | 2/2016 |
| JP | 2016039906 | A | 3/2016 |
| WO | 9714459 | A1 | 4/1997 |
| WO | 9800188 | A1 | 1/1998 |
| WO | 9907425 | A1 | 2/1999 |
| WO | 9909505 | A1 | 2/1999 |
| WO | 1999065548 | A1 | 12/1999 |
| WO | 02051473 | A1 | 7/2002 |
| WO | 02051476 | A1 | 7/2002 |
| WO | 02051477 | A1 | 7/2002 |
| WO | 02051479 | A1 | 7/2002 |
| WO | 02051481 | A1 | 7/2002 |
| WO | 02058766 | A1 | 8/2002 |
| WO | 02058767 | A1 | 8/2002 |
| WO | 03057283 | A1 | 7/2003 |
| WO | 03059422 | A1 | 7/2003 |
| WO | 2004028596 | A1 | 4/2004 |
| WO | 2005077441 | A2 | 8/2005 |
| WO | 2006045524 | A1 | 5/2006 |
| WO | 2006078400 | A1 | 7/2006 |
| WO | 2006108026 | A1 | 10/2006 |
| WO | 2007062315 | A2 | 5/2007 |
| WO | 2007079016 | A2 | 7/2007 |
| WO | 2005084732 | A1 | 11/2007 |
| WO | 2007126851 | A2 | 11/2007 |
| WO | 2007132353 | A1 | 11/2007 |
| WO | 2008024595 | A1 | 2/2008 |
| WO | 2008059233 | A1 | 5/2008 |
| WO | 2008064092 | A2 | 5/2008 |
| WO | 2008091838 | A1 | 7/2008 |
| WO | 2008091838 | A2 | 7/2008 |

| | | | |
|---|---|---|---|
| WO | 2009025996 | A1 | 2/2009 |
| WO | 2007032341 | A1 | 3/2009 |
| WO | 2009032400 | A1 | 3/2009 |
| WO | 2009081399 | A1 | 7/2009 |
| WO | 2009083600 | A1 | 7/2009 |
| WO | 2009140251 | A1 | 11/2009 |
| WO | 2009143255 | A1 | 11/2009 |
| WO | 2009144726 | A1 | 12/2009 |
| WO | 2010056712 | A1 | 5/2010 |
| WO | 2010076275 | A1 | 7/2010 |
| WO | 2010117923 | A1 | 10/2010 |
| WO | 2319564 | A2 | 5/2011 |
| WO | 2011067187 | A1 | 6/2011 |
| WO | 2011091246 | A2 | 7/2011 |
| WO | 2012032411 | A2 | 3/2012 |
| WO | 2012085031 | A1 | 6/2012 |
| WO | 2012145685 | A1 | 10/2012 |
| WO | 2012160156 | A2 | 11/2012 |
| WO | 2012160157 | A1 | 11/2012 |
| WO | 2012160159 | A1 | 11/2012 |
| WO | 2012160164 | A1 | 11/2012 |
| WO | 2012164389 | A2 | 12/2012 |
| WO | 2012164390 | A1 | 12/2012 |
| WO | 2012164394 | A2 | 12/2012 |
| WO | 2012164402 | A2 | 12/2012 |
| WO | 2012164403 | A2 | 12/2012 |
| WO | 2012164404 | A2 | 12/2012 |
| WO | 2012164406 | A2 | 12/2012 |
| WO | 2013004844 | A1 | 1/2013 |
| WO | 2013034985 | A2 | 3/2013 |
| WO | 2013034986 | A2 | 3/2013 |
| WO | 2013045617 | A1 | 4/2013 |
| WO | 2013070715 | A1 | 5/2013 |
| WO | 2011108225 | A1 | 6/2013 |
| WO | 2013079643 | A1 | 6/2013 |
| WO | 2013093059 | A1 | 6/2013 |
| WO | 2013126318 | A1 | 8/2013 |
| WO | 2014001318 | A2 | 1/2014 |
| WO | 2014001319 | A1 | 1/2014 |
| WO | 2014008393 | A1 | 1/2014 |
| WO | 2014019997 | A1 | 2/2014 |
| WO | 2014020000 | A1 | 2/2014 |
| WO | 2014020001 | A1 | 2/2014 |
| WO | 2014037946 | A1 | 3/2014 |
| WO | 2012066767 | A1 | 5/2014 |
| WO | 2014066256 | A1 | 5/2014 |
| WO | 2014083343 | A1 | 6/2014 |
| WO | 2014089083 | A1 | 6/2014 |
| WO | 2014089086 | A1 | 6/2014 |
| WO | 2014093107 | A1 | 6/2014 |
| WO | 2014124464 | A1 | 8/2014 |
| WO | 2014143815 | A2 | 9/2014 |
| WO | 2014144096 | A1 | 9/2014 |
| WO | 2014145535 | A2 | 9/2014 |
| WO | 2014164943 | A1 | 10/2014 |
| WO | 2014191355 | A1 | 12/2014 |
| WO | 2015022295 | A2 | 2/2015 |
| WO | 2013038639 | A1 | 3/2015 |
| WO | 2015066522 | A1 | 5/2015 |
| WO | 2015091555 | A1 | 6/2015 |
| WO | 2015144606 | A1 | 10/2015 |
| WO | 2015178961 | A1 | 11/2015 |
| WO | 2015179015 | A1 | 11/2015 |
| WO | 2015189700 | A1 | 12/2015 |
| WO | 2016003813 | A1 | 1/2016 |
| WO | 2016022865 | A1 | 2/2016 |
| WO | 2016025634 | A1 | 2/2016 |
| WO | 2016025934 | A1 | 2/2016 |
| WO | 2016040512 | A1 | 3/2016 |
| WO | 2016060908 | A1 | 4/2016 |
| WO | 2016060986 | A1 | 4/2016 |
| WO | 2016091978 | A1 | 6/2016 |
| WO | 2016099934 | A1 | 6/2016 |
| WO | 2016100781 | A1 | 6/2016 |
| WO | 2016115372 | A1 | 7/2016 |
| WO | 2015098399 | A1 | 3/2017 |
| WO | 2017212473 | A2 | 12/2017 |

* cited by examiner

SYSTEM AND METHOD FOR NEEDLE HIDING IN INJECTORS

REFERENCE TO RELATED APPLICATIONS

This application is a 371 of International Application No. PCT/IB2021/060507, filed Nov. 12, 2021, which claims priority to U.S. Provisional Application No. 63/114,008, file Nov. 16, 2020, the entirety of which are incorporated herein by reference.

Reference is hereby made to U.S. patent application Ser. No. 14/423,834, filed Sep. 3, 2013, which has published as US20150202367 and entitled "ELECTRONIC AUTO-INJECTION DEVICE", the disclosure of which is incorporated by reference in its entirety.

Reference is hereby additionally made to U.S. Provisional Patent Application 62/345,897, filed Jun. 6, 2016 and entitled "Electronic auto-injection device for drugs in cartridges", the disclosure of which is incorporated by reference in its entirety.

Reference is hereby made to a PCT Patent Application PCT/IL2017/050607, filed Jun. 1, 2017, which has published as WO2017212473 and entitled "Multiple use computerized injector", the disclosure of which is incorporated by reference in its entirety.

Reference is hereby additionally made to U.S. Provisional Patent Application 62/977,746, filed Feb. 18, 2020 and entitled "Multiple use computerized injector", the disclosure of which is incorporated by reference in its entirety.

Reference is hereby additionally made to U.S. Provisional Patent Application 63/052,562, filed Jul. 16, 2020 and entitled "SYSTEM AND METHOD FOR INFORMATION MANAGEMENT IN COMPUTERIZED INJECTORS", the disclosure of which is incorporated by reference in its entirety.

FIELD OF THE INVENTION

The present invention generally relates to a needle hiding feature in an injector, and more specifically to a needle hiding feature forming part of an injector, in particular a reusable, computerized injector, adapted for administration of medication to a patient.

BACKGROUND OF THE INVENTION

Many injectors, in particular reusable injectors and more particularly computerized injectors adapted for administration of medication to a patient are known. It is known that many users have a needle-phobia. Thus, it is advantageous to hide the needle at all times during the manipulation of the injector.

The invention relates more particularly to an injector comprising a housing arranged along a longitudinal axis and configured to receive a medicament cartridge; an injection drive mechanism for driving a piston, the piston forming part of the medicament cartridge, the injection drive mechanism injecting a medicament when the piston is forwardly displaced; and a needle hiding element, which is slidably attached to the housing.

In reusable injectors of this type, the user typically needs to attach a needle at the distal end of the injector before proceeding to the injection and also detach the needle after use. This operation is rendered rather difficult due to the presence of the needle hiding element as the user needs to retract the needle hiding element and maintain it in a retracted position against the action of a biasing spring, while attaching the needle. Similar handling is required to detach the needle.

An object of the invention is to facilitate the operations of attaching and detaching the needle.

SUMMARY OF THE INVENTION

The present invention seeks to provide an injector with a needle hiding element, that is easy to handle for attaching or detaching a needle.

There is thus provided in accordance with an embodiment of the present invention an injector, comprising a housing arranged along a longitudinal axis and configured to receive a medicament cartridge; an injection drive mechanism for driving a piston, the piston forming part of the medicament cartridge, the injection drive mechanism injecting a medicament when the piston is forwardly displaced; and a needle hiding element, which is slidably attached to the housing and positionable in at least one of an extended orientation and a retracted orientation, wherein in the extended orientation the needle hiding element protrudes forwardly from the housing and in the retracted orientation, the needle hiding element is locked relative to the housing.

The user can thus selectively place the needle hiding element, by manually acting thereon, either in a retracted stable position, such that a needle can be easily attached or detached, or in fully extended position, such that the device is ready for use when a needle is attached.

Preferably, in the extended orientation the needle hiding element is slidable relative to the housing and in the retracted orientation the needle hiding element does not protrude forwardly from the housing or protrudes to a lesser extent than in the extended orientation.

Further preferably, the needle hiding element is also positionable in a partially retracted orientation, in which the needle hiding element protrudes forwardly from the housing to a greater extent than in the retracted orientation and is slidably moveable relative to the housing.

Still further preferably, the needle hiding element is biased to be displaced forwardly under the urge of at least one biasing element, which is supported between the housing and the needle hiding element.

According to a preferred embodiment, the needle hiding element includes at least a flexible arm, extending axially and comprising a snap-fit locking feature that can be engaged in a corresponding feature provided on the housing and a racially protruding button that can be handled by a user for deflecting the arm and axially moving the needle hiding element, whereby the user can position the needle hiding element in one of said extended and retracted orientations.

Preferably, the snap-fit locking feature of the flexible arm and the corresponding feature of the housing are designed to provide the locked retracted orientation of the needle hiding element, that can be unlocked by the user by pressing on the button whereby the locking feature of the arm is disengaged from the corresponding feature of the housing.

Still further preferably, the needle hiding element includes a pair of opposing flexible arms, each provided with a snap-fit locking feature and a button, whereby the locked retracted orientation of the needle hiding element can be unlocked by the user by simultaneously pressing on the buttons for simultaneous deflection of the arms.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS OF THE INVENTION

An injector according to the invention and illustrated on the Figures comprises a housing arranged along a longitudinal axis and configured to receive a medicament cartridge; an injection drive mechanism for driving a piston, forming part of the medicament cartridge, for injecting a medicament. The injector also comprises a needle hiding element, forming part of the injector. The needle hiding element is biased to an extended orientation, in which the needle is covered, and being selectively lockable in a retracted orientation, in which the needle is exposed. It is noted that the drive mechanism can be either one of manual, mechanical or electrical and the injector preferably includes a computer-controlled motor.

In the present description, the term “orientation” relating to the needle hiding element, for example in the expressions “[retracted or extended] orientation” or “operative orientation”, shall be understood as referring to the axial position of the needle hiding element.

Figure 1:
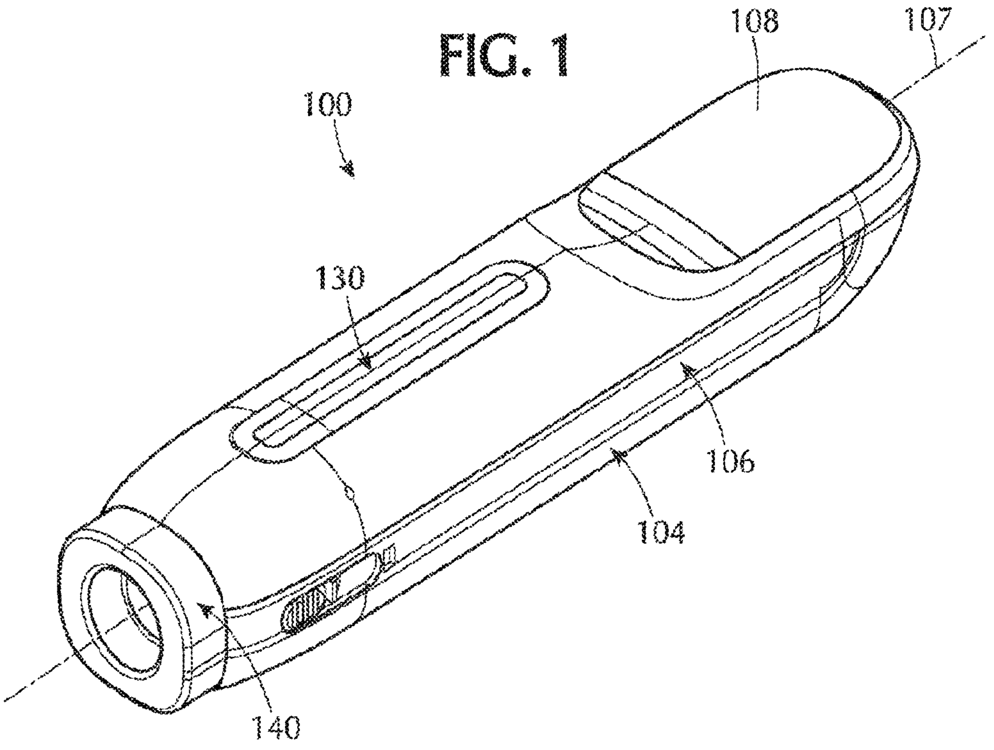
FIG. 1 is a simplified pictorial illustration of an injector constructed and operative in accordance with an embodiment of the present invention and shown in a closed operative orientation.
Figure 2A:
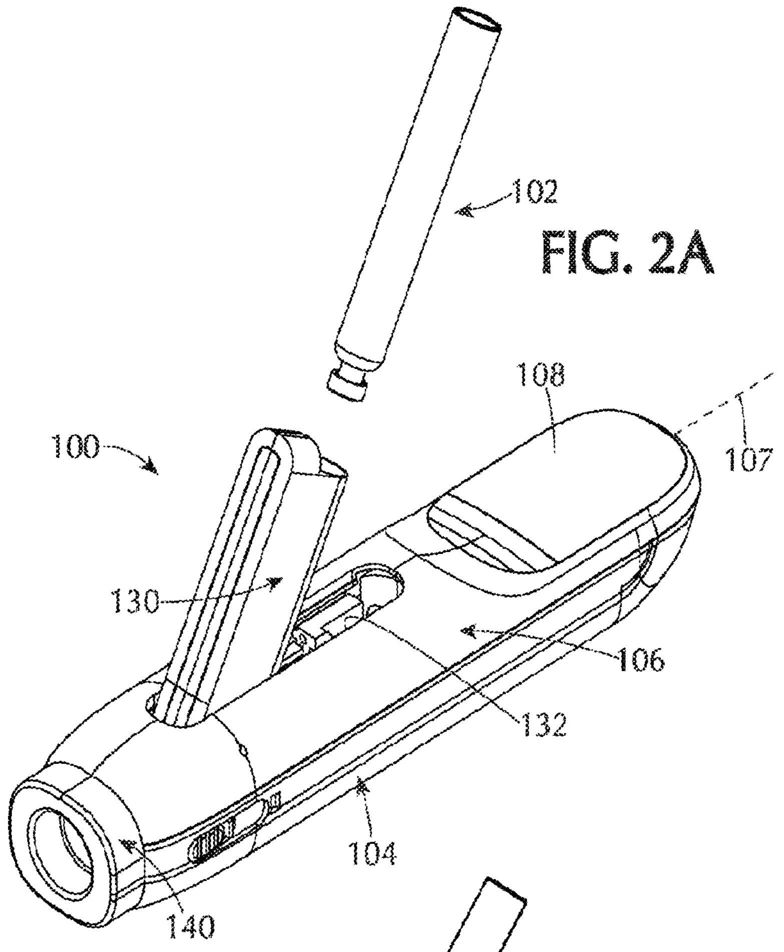
FIGS. 2A and 2B are simplified respective pictorial and side planar view illustrations of the injector of FIG. 1 shown in an open operative orientation.
Figure 2B:
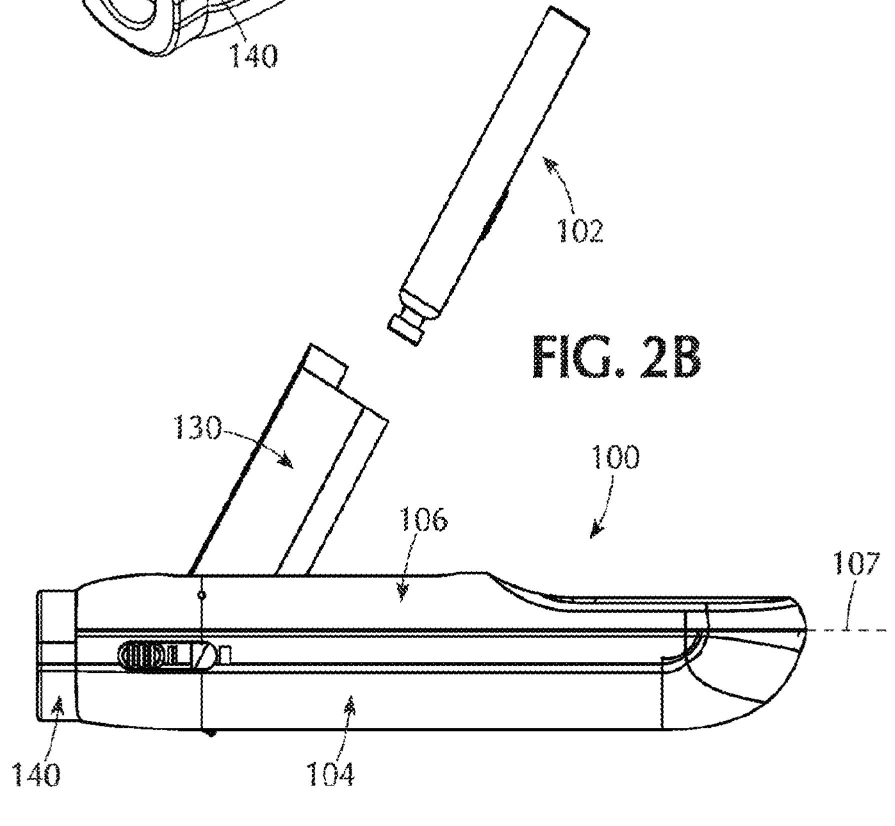
Figure 3:
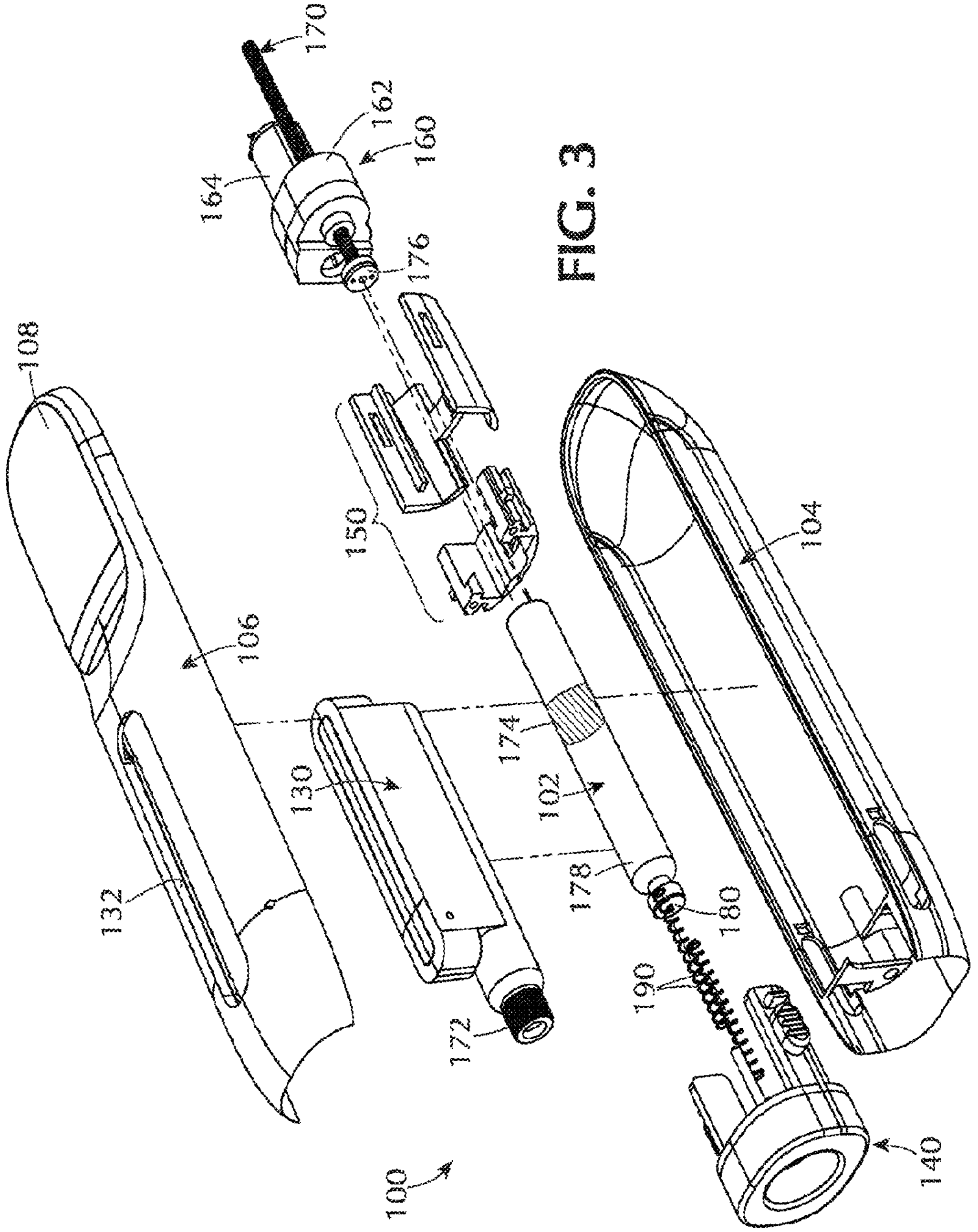
FIG. 3 is a simplified exploded view illustration of the injector of FIGS. 1-2B.

Reference is now made to FIG. 1, which is a simplified pictorial illustration of an injector constructed and operative in accordance with an embodiment of the present invention and shown in a closed operative orientation and to FIGS. 2A and 2B, which are simplified respective pictorial and side planar view illustrations of the injector of FIG. 1 shown in an open operative orientation. Reference is additionally made to FIG. 3, which is a simplified exploded view illustration of the injector 100 of FIGS. 1-2B.

An injector for cartridge insertion 100 is seen in FIGS. 1-3. The injector 100 is shown in a closed operative orientation in FIG. 1 and in an open operative orientation in FIGS. 2A and 2B, just prior to insertion of a medicament cartridge 102 thereinto.

It is seen in FIGS. 1-3 that the injector 100 includes a housing comprising a top housing portion 106 and a bottom housing portion 104, fixedly coupled thereto, both arranged along a mutual longitudinal axis 107. A display 108 is preferably disposed within the injector 100 formed in the top housing portion 106.

It is also seen particularly in FIGS. 2A-3 that a cartridge enclosure assembly 130 is mounted through an opening 132 formed in top housing portion 106 and is configured to be pivotably mounted with respect to top housing portion 106.

It is a particular feature of an embodiment of the present invention that a selectively lockable needle hiding element 140 is mounted to the forward (or distal) end of the injector 100 and is at least partially inserted into the enclosure volume formed between the top housing portion 106 and the bottom housing portion 104. It is noted that the needle hiding element 140 is slidably moveable with respect to the housing portions 104 and 106 and is selectively lockable in a rearward (or proximal) position in some of the operative orientations as described in detail hereinbelow.

It is particularly seen in FIG. 3 that a chassis assembly 150 is residing within the enclosure formed between the top housing portion 106 and the bottom housing portion 104. The chassis assembly 150 is configured to support the internal components of the injector 100. A drive assembly 160 is preferably supported on the chassis assembly 150. The drive assembly preferably includes an electrical motor 162, powered by a battery 164 and configured for axially displacing a plunger rod 170 along the longitudinal axis 107.

It is seen in FIG. 3 that the cartridge enclosure assembly 130 is residing between the housing portions 104 and 106. The cartridge enclosure assembly 130 is adapted to receive the medicament cartridge 102 therewithin and is generally pivotably mounted with respect to the housing portions 104 and 106. The cartridge enclosure assembly 130 is configured to be biased to an open operative orientation with respect to housing portions 104 and 106. The cartridge enclosure assembly 130 includes a forward generally externally threaded end 172, adapted for engagement of a needle assembly therewith.

It is noted that a piston 174 is disposed within the medicament cartridge 102 and confines a medicament within the medicament cartridge 102. The plunger rod 170 is configured to displace the piston 174 within the medicament cartridge 102 following receipt of a suitable signal from the CPU of the injector 100 to effect ejection of medication therefrom.

It is seen in FIG. 3 that a piston contact element 176 is mounted onto the forward end of plunger rod 170 and is configured to engage the piston 174 in certain operative orientations of the injector 100, as described in detail hereinebelow.

The medicament cartridge 102 has a generally cylindrical barrel 178 with a forward end including a resilient septum 180. A medicament is contained within the cylindrical barrel 178 and is sealed therewithin by piston 174. The cylindrical barrel 102 is arranged along the longitudinal axis 107.

It is noted that any type of medicament container may be employed as part of an embodiment of the present invention, such as for example, pre-filled cartridges containing a liquid medication, dual-chamber cartridges containing a powder drug preparation and a solvent or any other suitable medicament cartridge 102.

It is further noted that the particular spatial relationships between the various components of the injector 100 are preferably similar to the spatial relationships as described in PCT patent application PCT/IL2017/050607, which is incorporated by reference herein in its entirety.

It is a particular feature of an embodiment of the present invention that the needle hiding element 140 is biased forwardly under the urge of springs 190, which are supported between the needle hiding element 140 and the housing portions 104 and 106.

Reference is now made to FIGS. 4A, 4B, 4C and 4D, which are simplified respective pictorial, rear planar view, side planar view and front planar view of the top housing portion 106 of the injector 100 of FIGS. 1-3.

The top housing portion 106 is an integrally formed element arranged along longitudinal axis 107 and having display portion 108 and opening 132 for mounting of the cartridge enclosure assembly 130 therethrough. The top housing portion 108 has a forward end 200 and a rearward end 202. An opening 203 is formed at the forward end 200.

Figure 4A:
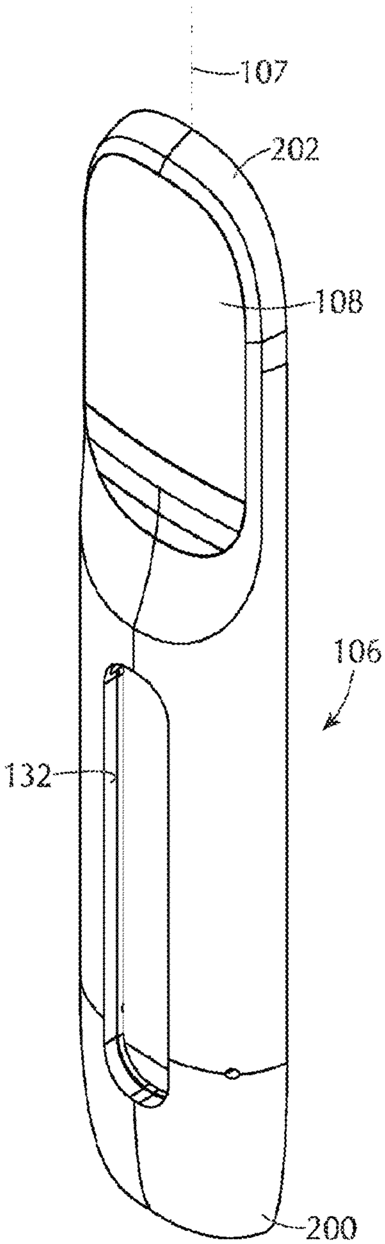
FIGS. 4A, 4B, 4C and 4D are simplified respective pictorial, rear planar view, side planar view and front planar view of a top housing portion of the injector of FIGS. 1-3.
Figure 4B:
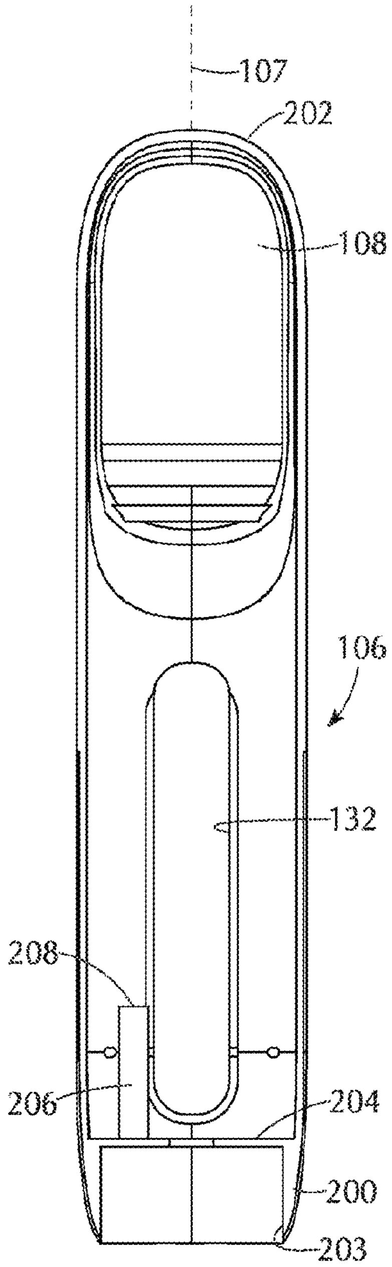
Figure 4C:
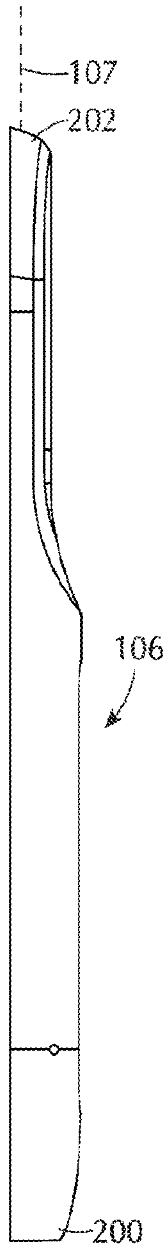
Figure 4D:
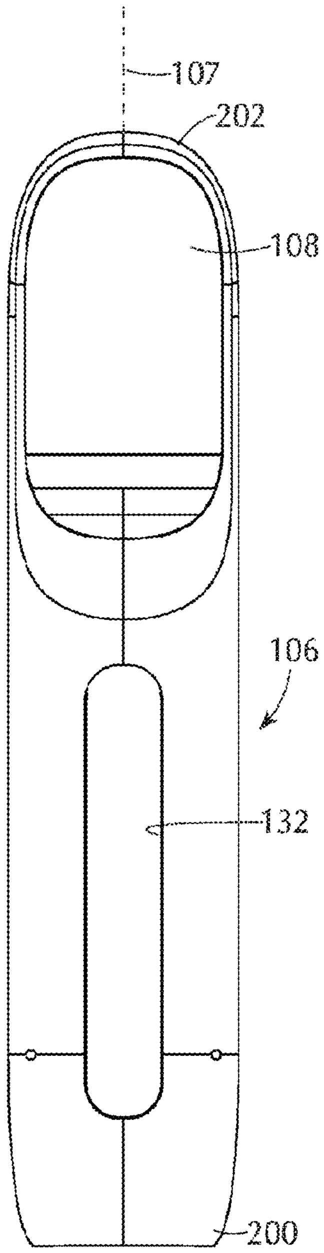

It is seen specifically in FIG. 4B that a flange 204 is disposed adjacent the forward end 200, the flange 204 generally extends transversely to the longitudinal axis 107. A generally cylindrical hollow longitudinal protrusion 206, which serves as a spring enclosure, extends rearwardly from the flange 204 and has a closed rearward end 208, serving as a spring stop.

Figure 5C:
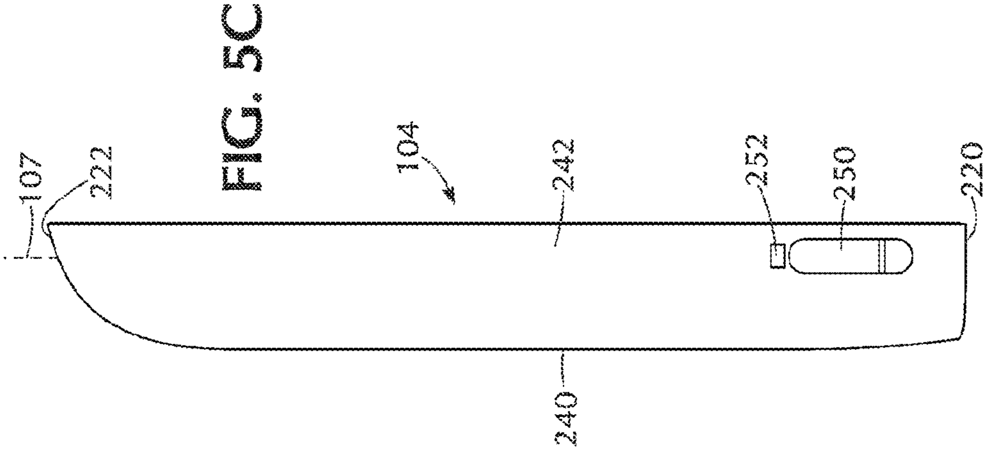
FIGS. 5A, 5B and 5C are simplified respective pictorial, rear planar view and side planar view of a bottom housing portion of the injector of FIGS. 1-3.
Figure 5B:
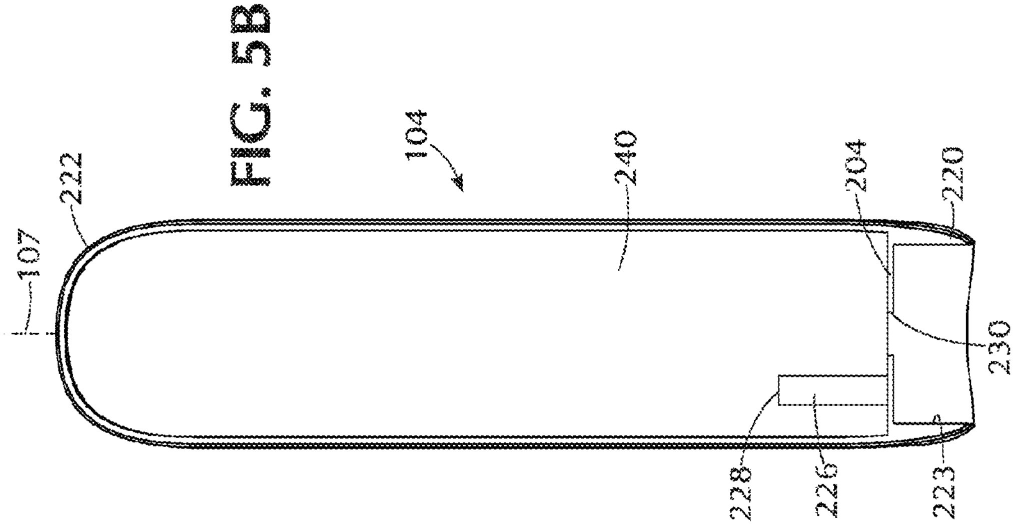
Figure 5A:
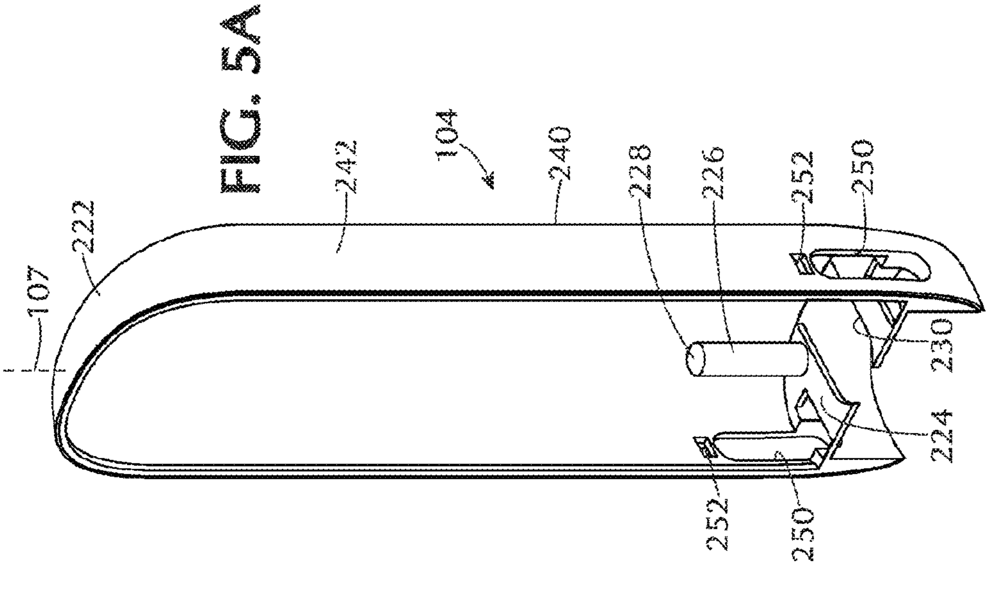

Reference is now made to FIGS. 5A, 58 and 5C, which are simplified respective pictorial, rear planar view and side planar view of the bottom housing portion 104 of the injector 100 of FIGS. 1-3.

The bottom housing portion 104 is an integrally formed element arranged along longitudinal axis 107 and having a forward end 220 and a rearward end 222. An opening 223 is formed at the forward end 220.

It is seen specifically in FIGS. 5A and 5B that a flange 224 is disposed adjacent the forward end 220, the flange 224 generally extends transversely to the longitudinal axis 107. A generally cylindrical hollow longitudinal protrusion 226, which serves as a spring enclosure, extends rearwardly from the flange 224 and has a closed rearward end 228, serving as a spring stop. The flange 224 also includes a cut-out 230 for insertion of a portion of the cartridge enclosure assembly 130 therethrough.

The bottom housing portion 104 defines a generally concave back wall 240 joined with two side walls 242 on two opposite sides thereof.

It is seen in FIGS. 5A and 5C that typically two longitudinal cut-outs 250 are formed on the side walls 242 of the bottom housing portion 104, the cut-outs 250 generally disposed adjacent the forward end 220 thereof. Typically, a relatively small snap cut-out 252 is formed adjacent each one of the cut-outs 250 and is slightly rearwardly spaced therefrom.

It is noted that alternatively, a single cut-out, equivalent to cut-out 250 may be formed on the back wall 240 of the bottom housing portion 104 and a relatively small snap cut-out, equivalent to snap cut-out 252 may be formed rearwardly thereof on the back wall 240. Further alternatively, any other number of such cut-outs may be formed at any other location on the bottom housing portion 104.

Figure 6A:
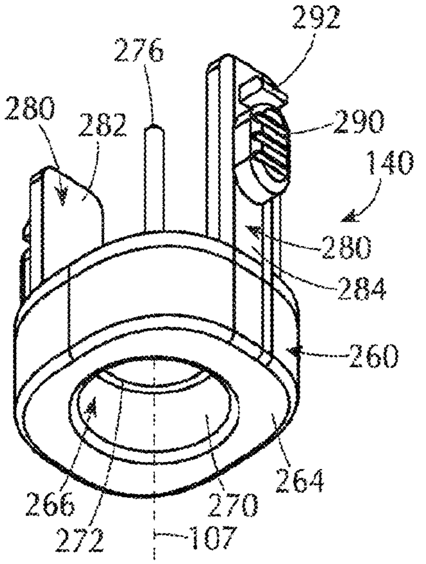
FIGS. 6A, 6B, 6C, 6D, 6E, 6F and 6G are simplified respective two pictorials views taken from different perspectives, two side planar views, top planar view, bottom planar view and a section view of a needle hiding element of the injector of FIGS. 1-3, section view being taken along lines G-G in FIG. 6F.
Figure 6B:
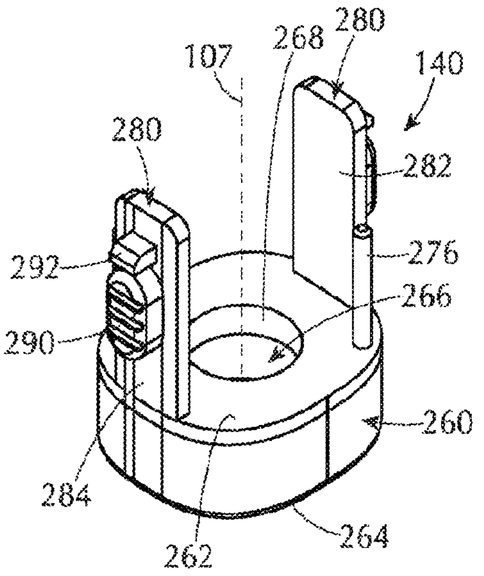
Figure 6C:
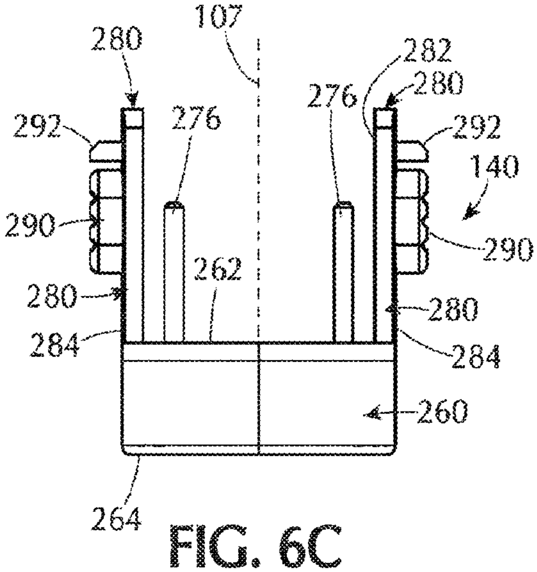
Figure 6D:
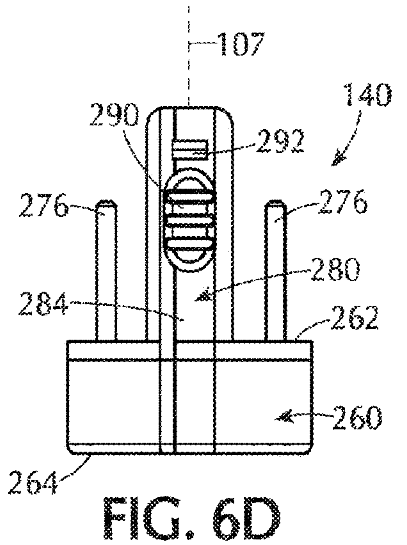
Figure 6E:
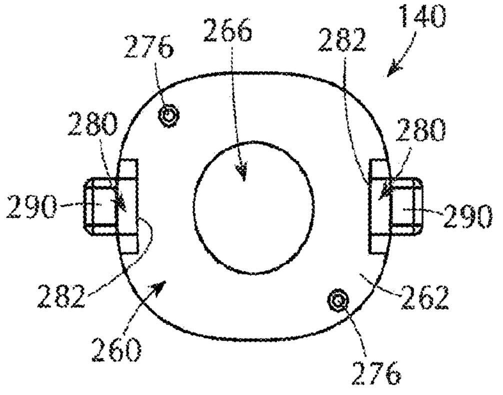
Figure 6F:
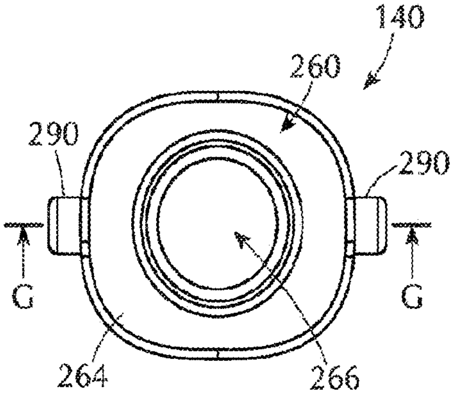
Figure 6G:
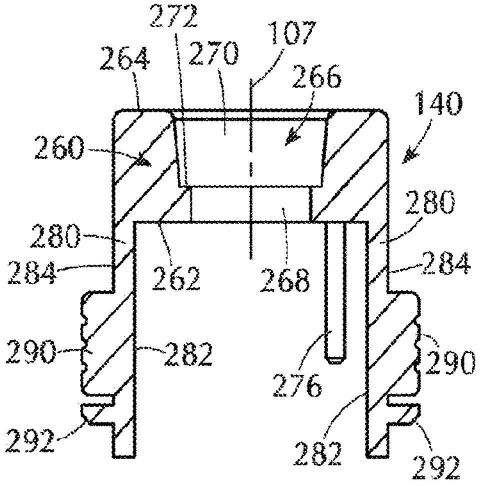

Reference is now made to FIGS. 6A, 6B, 6C, 6D, 6E, 6F and 6G, which are simplified respective two pictorials views taken from different perspectives, two side planar views, top planar view, bottom planar view and a section view of the needle hiding element 140 of the injector 100 of FIGS. 1-3, section view being taken along lines G-G in FIG. 6F.

The needle hiding element 140 is an integrally formed element arranged along longitudinal axis 107. The needle hiding element 140 has a base wall portion 260 defining a rearwardly facing surface 262 and a forwardly facing surface 264. The base wall portion 260 also has a substantially cylindrical section, axially extending between the rearwardly and forwardly facing surfaces 262, 264, and is designed to at least partially enclose a needle attached to the cartridge 102, in particular to hide and prevent access to the tip of the needle. An opening 266 is formed through the base wall portion 260. The opening 266 has a cylindrical portion 268 extending forwardly from the rearwardly facing surface 262 and a forwardly tapered conical portion 270 extending forwardly of the cylindrical portion 268 and up to the forwardly facing surface 264. A forwardly facing shoulder 272 is formed between the cylindrical portion 268 and the conical portion 270.

Typically, two guiding pins 276 extend rearwardly from the rearwardly facing surface 262 and are disposed generally diagonally with respect to each other.

Typically, two mounting arms 280 mutually facing each other, extend axially and rearwardly from the base wall portion 260 and define an inwardly facing surface 282 and an outwardly facing surface 284. A button 290 is formed on the outwardly facing surface 284 of each of the mounting arms 280 and a snap protrusion 292 is also formed on the outwardly facing surface 284 and is slightly rearwardly spaced from button 290. The buttons 290 preferably define an outer surface with an array of small protrusions or a like to assist with gripping by the user. The axially extending arms 280 are spaced from the axis 107 and provided at opposing locations with respect to the axis. Each one of the opposing arms 280 is flexible and can be resiliently deflected by exerting a radial pressure thereon. Each snap protrusion 292 defines a snap-fit locking feature that can be engaged in a corresponding feature, the snap cut-out 252, provided on the housing. Each button 290 is radially protruding and can be handled by a user for deflecting the arm 280 and for axially moving the needle hiding element 140 with respect to the housing 104, 106, whereby the user can position the needle hiding element 140 in an extended or in a retracted position with respect to the housing.

It is noted that alternatively a single mounting arm or any other number of mounting arms may be formed as part of the needle hiding element 140, all according to an embodiment of the present invention.

Figure 7:
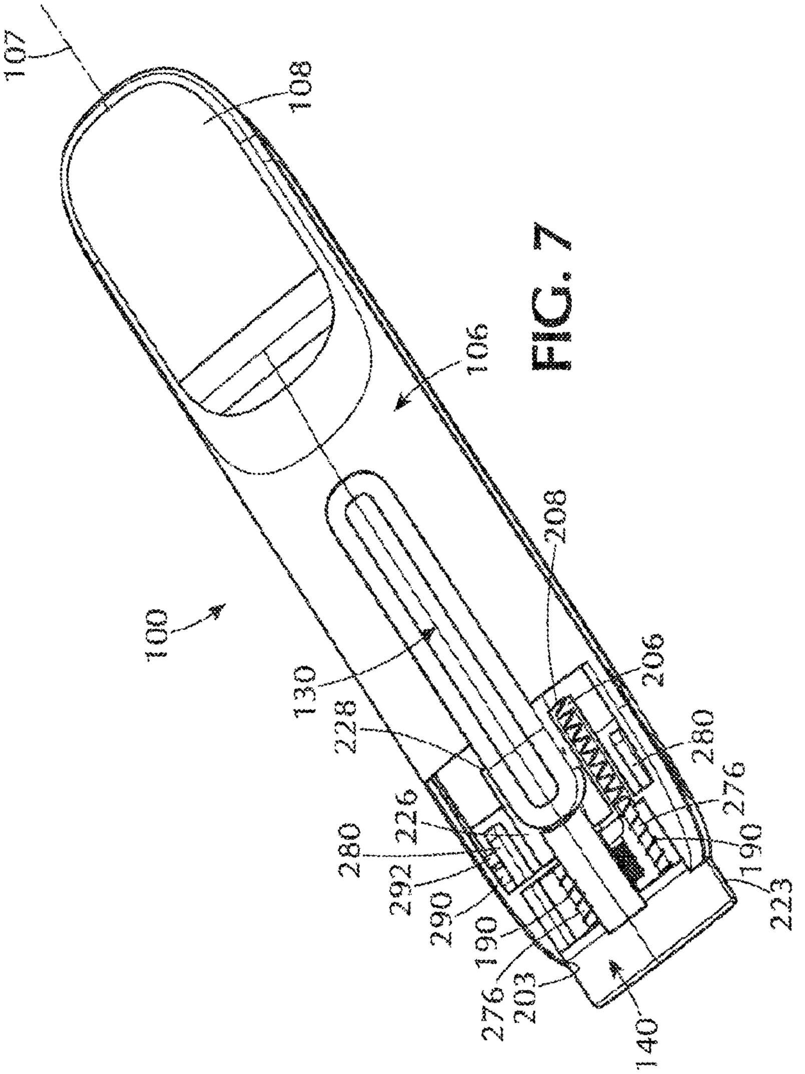
FIG. 7 is a simplified pictorial partially cut-out illustration, showing a portion of the needle hiding element of FIGS. 6A-6G as part of the assembled injector of FIGS. 1-3.

Reference is now made to FIG. 7, which is a simplified pictorial partially cut-out illustration, showing a portion of the needle hiding element 140 of FIGS. 6A-6G as part of the assembled injector 100 of FIGS. 1-3.

The assembled injector 100 is seen in FIG. 7. It is particularly seen that the needle hiding element 140 is partially inserted into the enclosure formed by the upper housing portion 106 and the bottom housing portion 104, through their respective openings 203 and 223.

The guiding pins 276 of the needle hiding element 140 are axially aligned with protrusion 206 of the upper housing portion 106 and protrusion 226 of the bottom housing portion 104. One of the biasing springs 190 is mounted onto one of the guiding pins 276 and is supported against the closed end 208 of protrusion 206 of the upper housing portion 106. The other biasing spring 190 is mounted onto another one of the guiding pins 276 and is supported against the closed end 228 of protrusion 226 of the bottom housing portion 104.

It is noted that alternatively, any other number of biasing springs 190 supported in any other suitable manner may be employed in accordance with an embodiment of the present invention.

It is noted that the forward portion of the injector is cut-out in two different plane to clarify the position of both biasing springs 190, since the springs 190 are disposed diagonally with respect to each other and thus lay in two different planes.

The springs 190 are configured to bias the needle housing element 140 forwardly along longitudinal axis 107, relative to the housing portions 104 and 106.

It is seen in FIG. 7 that the springs 190 are in a non-stressed orientation (i.e. non-stressed or non-compressed state), biasing the needle hiding element 140 fully forwardly.

Figure 8A:
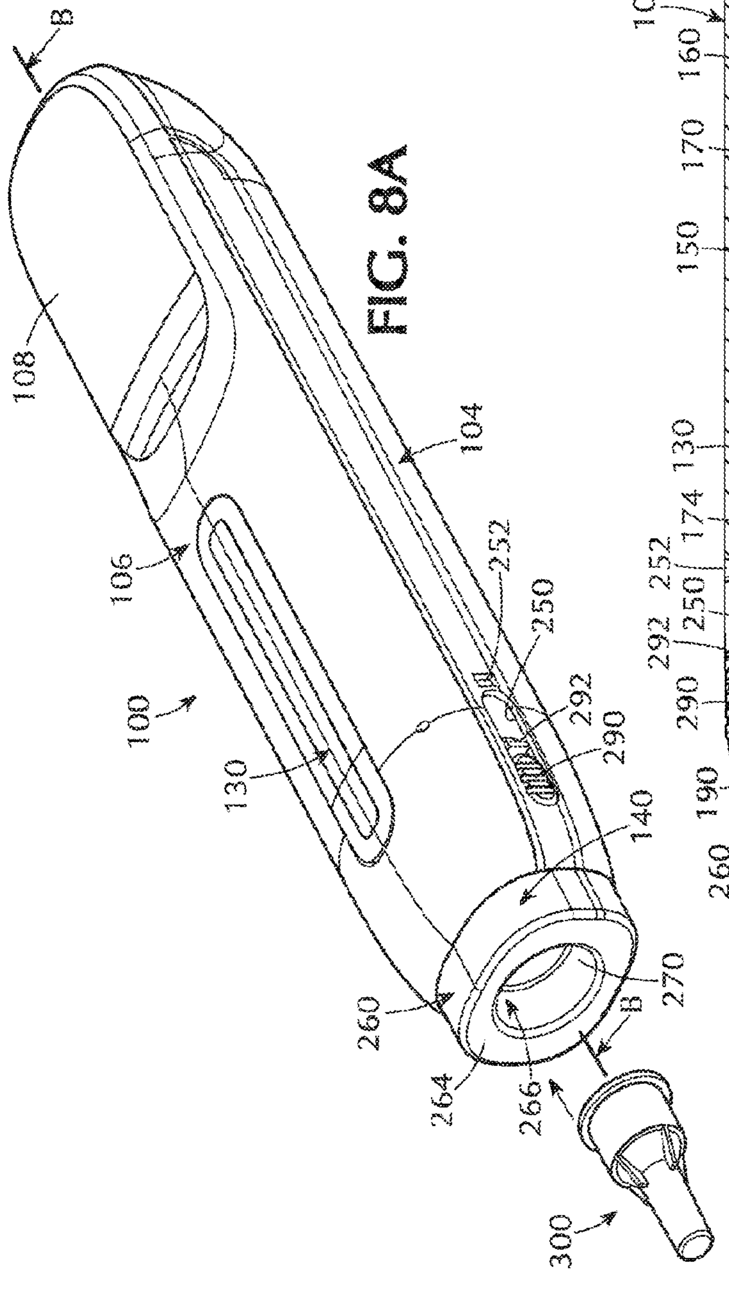
FIGS. 8A and 8B are simplified respective pictorial and section view illustrations of the injector of FIGS. 1-3 operated by a user, in a needle attachment operative orientation, section view being taken along lines B-B in FIG. 8A.
Figure 8B:
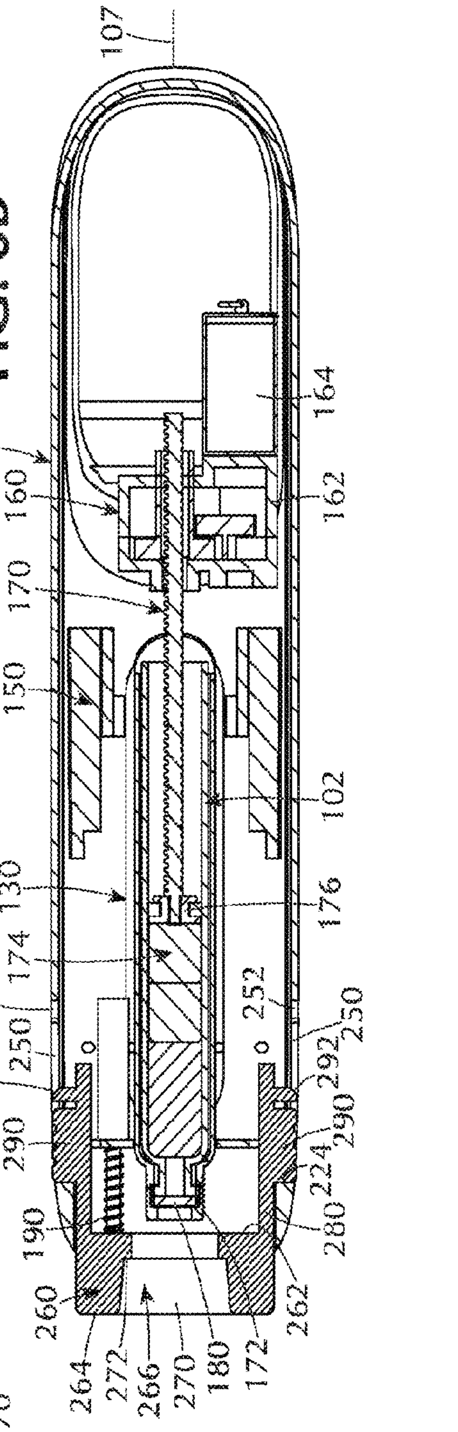

Reference is now made to FIGS. 8A and 8B, which are simplified respective pictorial and section view illustrations of the injector 100 of FIGS. 1-3 operated by a user, in a needle attachment operative orientation, section view being taken along lines B-B in FIG. 8A.

The injector 100 is seen in storage in FIGS. 8A and 8B, prior to attachment of a needle assembly 300 to the externally threaded end 172 of the cartridge enclosure assembly 130.

It is seen in FIGS. 8A and 8B that the needle hiding element 140 is partially inserted into the forward end of the housing portions 104 and 106 of the injector 100 and is biased forwardly along longitudinal axis 107 under the urge of biasing springs 190, as specifically described with reference to FIG. 7.

It is a particular feature of an embodiment of the present invention that the needle hiding element 140 is non-releasably slidably mounted onto the housing portions 104 and 106 and is slidably displaceable with respect thereto. Particularly, buttons 290 and the snap protrusions 292 of the needle hiding element 140 are seated within cut-outs 250 of the bottom housing portion 104 in the storage operative orientation, before the attachment of the needle assembly 300 to the injector 100.

It is particularly seen in FIG. 8B that buttons 290 of the needle hiding element 140 are supported against the forward ends of cut-outs 250 of the bottom housing portion 104, and thus the needle hiding element 140 is restrained from forward displacement along longitudinal axis 107 relative to the housing portions 104 and 106 and removal therefrom.

It is seen that in this storage operative orientation, the biasing springs 190 are disposed in their non-stressed operative orientation, thus biasing the needle hiding element 140 to its forward position, in which the needle hiding element 140 extends forwardly from the forward end 200 and 220 of the upper and bottom housing portions respectively, such that the forwardly facing surface 264 of the needle hiding element 140 is forwardly spaced from the forward ends 200 and 220.

It is particularly seen that the buttons 290 of the needle hiding element 140 are disposed at the forward end of the cut-outs 250 of the bottom housing portion 104 and the snap protrusions 292 are forwardly spaced from the snap cut-outs 252 in the bottom housing portion 104.

It is also seen in FIG. 8B that the medicament is confined within the medicament cartridge 102 by means of the piston 174 and the piston contact element 176 of the plunger rod 170 engages the piston 174. The drive assembly 160 that drives the plunger rod 170 along the longitudinal axis 107 is preferably similar in all respects to the one described in PCT patent application PCT/IL2017/050607, which is incorporated by reference herein in its entirety.

Figure 9A:
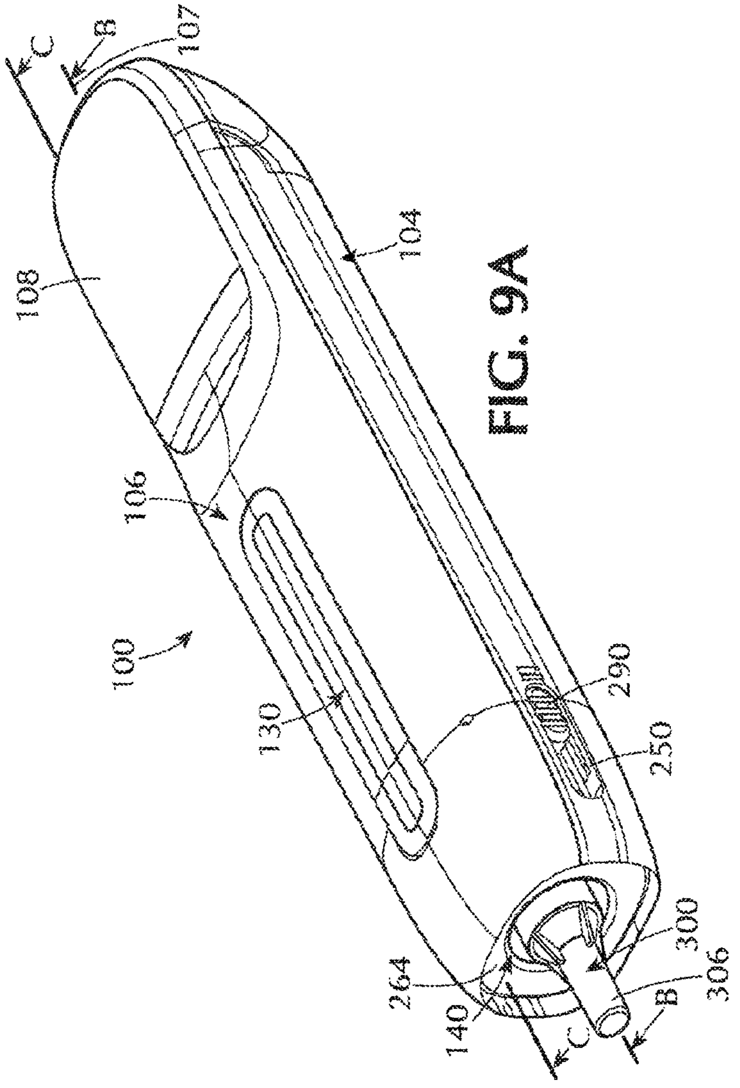
FIGS. 9A, 9B and 9C are simplified respective pictorial and two section view illustrations of the injector of FIGS. 1-3 operated by a user, in a needle attached operative orientation, section views being taken along lines B-B and C-C respectively in FIG. 9A.
Figure 9B:
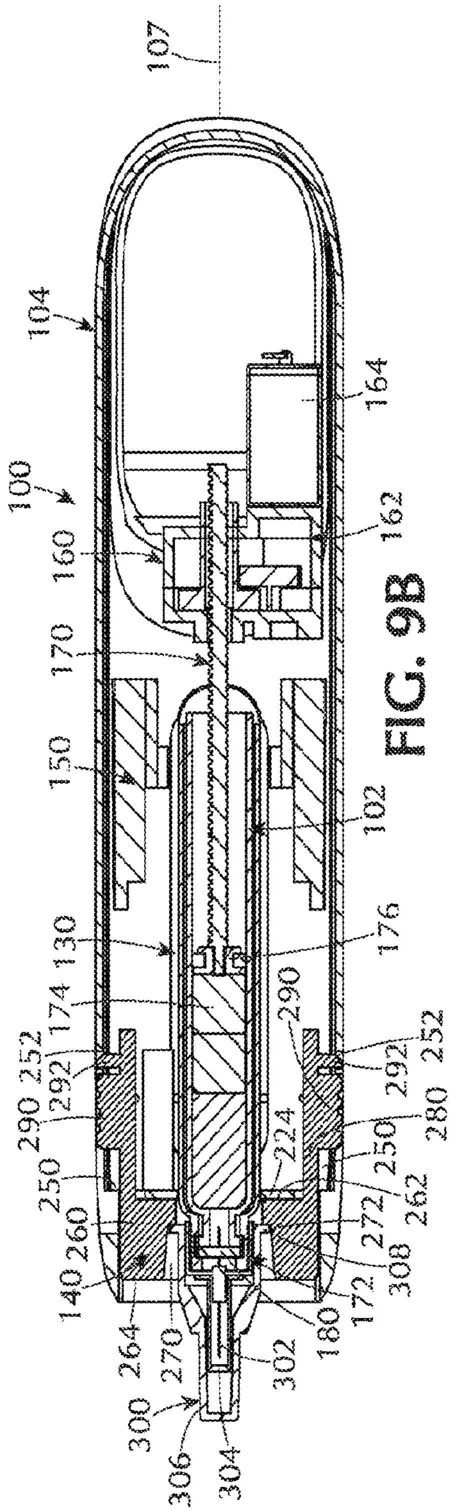
Figure 9C:
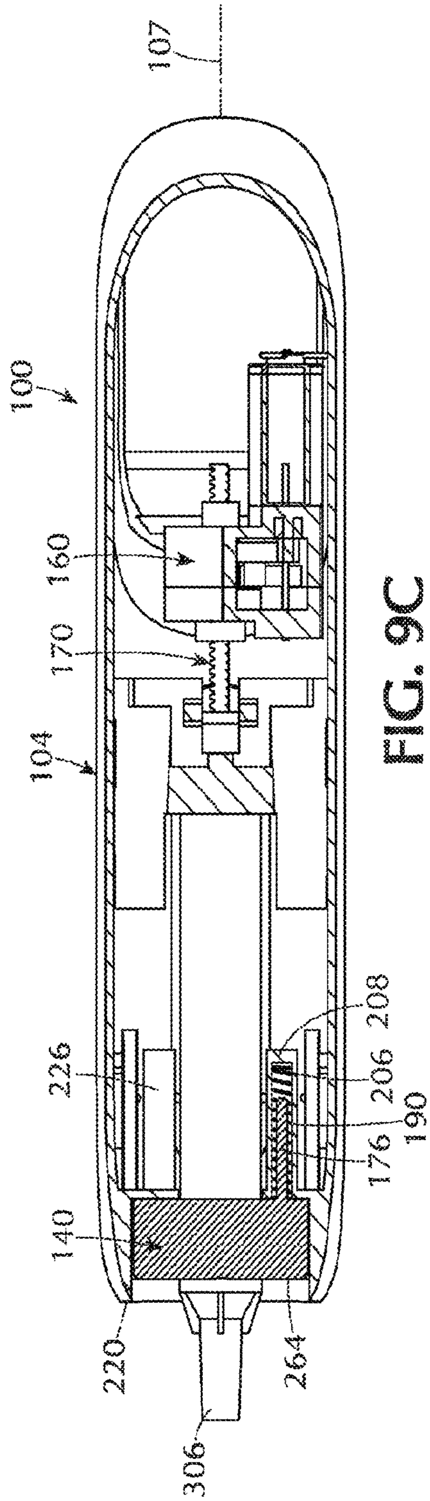

Reference is now made to FIGS. 9A, 9B and 9C, which are simplified respective pictorial and two section view illustrations of the injector 100 of FIGS. 1-3 operated by a user, in a needle attached operative orientation, section views being taken along lines B-B and C-C respectively in FIG. 9A.

The injector 100 is seen in needle attached operative orientation in FIGS. 9A-9C, following attachment of the needle assembly 300 to the externally threaded end 172 of the cartridge enclosure assembly 130. It is seen particularly in FIG. 9B that the needle assembly 300 preferably includes a needle 302, attached to a needle hub having an internal threading, that is adapted to be threaded onto the externally threaded end 172 of the cartridge enclosure assembly 130. Preferably, an internal needle cap 304 is mounted onto the needle 302 and an outer needle cap 306 is mounted over the internal needle cap 304 and over the needle hub. The outer needle cap 306 includes a circumferential rear end 308.

It is seen particularly in FIG. 9B that upon attachment of the needle assembly 300 to the injector 100, the needle 302 with the needle hub is threadably attached to the externally threaded end 172 of the cartridge enclosure assembly 130, thereby engaging the circumferential rear end 308 of the outer needle cap 306 with the forwardly facing shoulder 272 of the needle hiding element 140. Engagement of the outer needle cap 306 with the needle hiding element 140 causes rearward slidable displacement of the needle hiding element 140 relative to the housing portions 104 and 106 against the urge of the biasing springs 190.

It is seen in FIGS. 9A-9C that the needle hiding element 140 is now disposed within the enclosure formed by the housing portions 104 and 106, such that the forwardly facing surface 264 of the needle hiding element 140 is rearwardly spaced from the forward ends 200 and 220 of housing portions 106 and 104 respectively.

It is a particular feature of an embodiment of the present invention that the needle 302 in this needle attached operative orientation is covered by the internal needle cap 304 and the outer needle cap 306 and the needle hiding element 140 is disposed in a retracted locked orientation, which is the rearwardmost position of the needle hiding element 140. It is specifically seen in FIG. 9B that in this retracted locked orientation of the needle hiding element 140, the snap protrusions 252 are rearwardly displaced relative to the housing portions 104 and 106 and are now inserted into snap cut-outs 292 of the bottom housing portion 104 and the buttons 290 are positioned adjacent the rearward ends of the cut-outs 250. The needle hiding element 140 is temporarily locked in its retracted position and is restrained from forward longitudinal displacement along longitudinal axis 107 by means of engagement between snap protrusions 292 with snap cut-outs 252. The locking of the snap protrusions 292 with snap cut-outs 252 is enabled due to temporary inward deflection of the mounting arms 280 of the needle hiding element 140.

It is also seen particularly in FIG. 9C that the biasing springs 190 are now disposed in a compressed operative orientation, but are prevented from displacing the needle hiding element 140 forwardly due to the locking engagement of the snap protrusions 292 with the snap cut-outs 252.

It is particularly seen in FIG. 9B that buttons 290 of the needle hiding element 140 are rearwardly spaced from the forward end of cut-outs 250 of the bottom housing portion 104.

It is also seen in FIG. 9B that the medicament is confined within the medicament cartridge 102 by means of the piston 174 and the piston contact element 176 of the plunger rod 170 engages the piston 174. The drive assembly 160 that drives the plunger rod 170 along the longitudinal axis 107 is preferably similar in all respects to the one described in PCT patent application PCT/IL2017/050607, which is incorporated by reference herein in its entirety.

It is also seen in FIG. 9B that the needle 302 now penetrates the septum 180 of the medicament cartridge 102 and thus is disposed in fluid communication with the medicament confined within the medicament cartridge 102.

It will be appreciated that, during the operation of attaching the needle, the temporary locking of the needle hiding element 140 in the retracted position, caused by the engagement of the snap protrusions 292 with the corresponding snap cut-outs 252, facilitates the completion of the operation as the user does not need to maintain the needle hiding element against the biasing force of the springs 190. While the operation of attaching the needle that has been described involves a step of pushing the needle hiding element 140 backwards with the outer needle cap 306, the user may alternatively act on the buttons 290 to manually move the needle hiding element 140 to the locked retracted position prior to engaging the needle assembly 300.

Figure 10A:
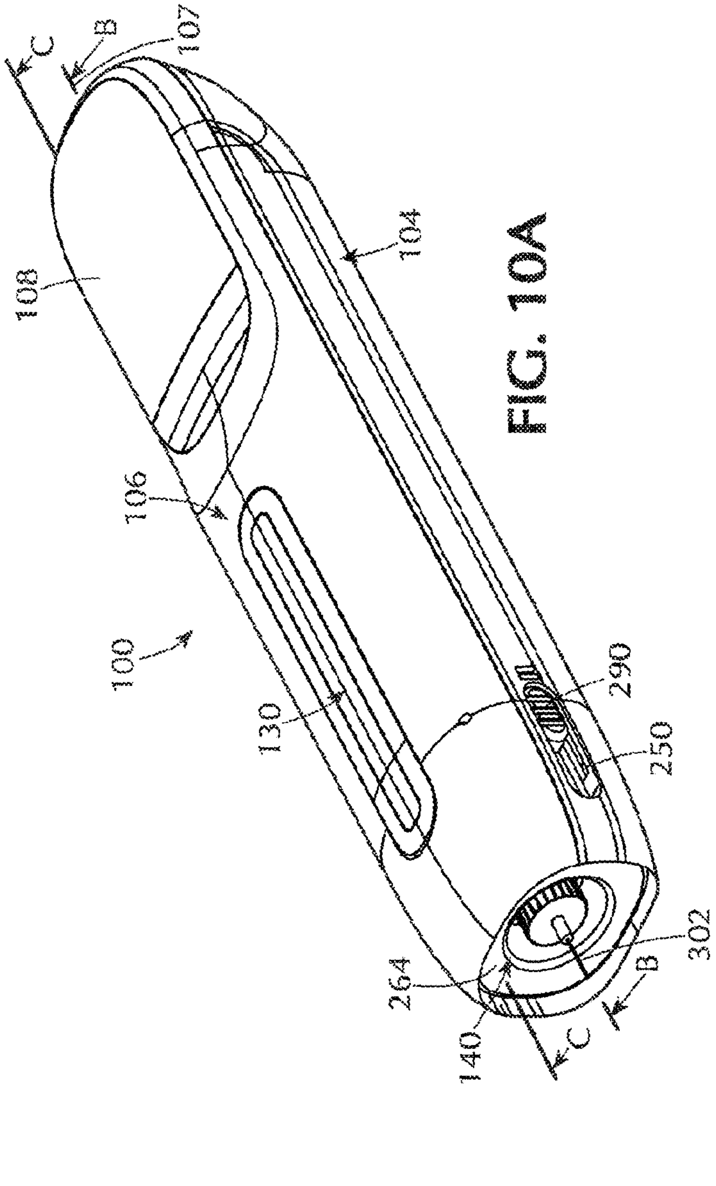
FIGS. 10A, 10B and 10C are simplified respective pictorial and two section view illustrations of the injector of FIGS. 1-3 operated by a user, in a needle exposure operative orientation, section views being taken along lines B-B and C-C respectively in FIG. 10A.
Figure 10B:
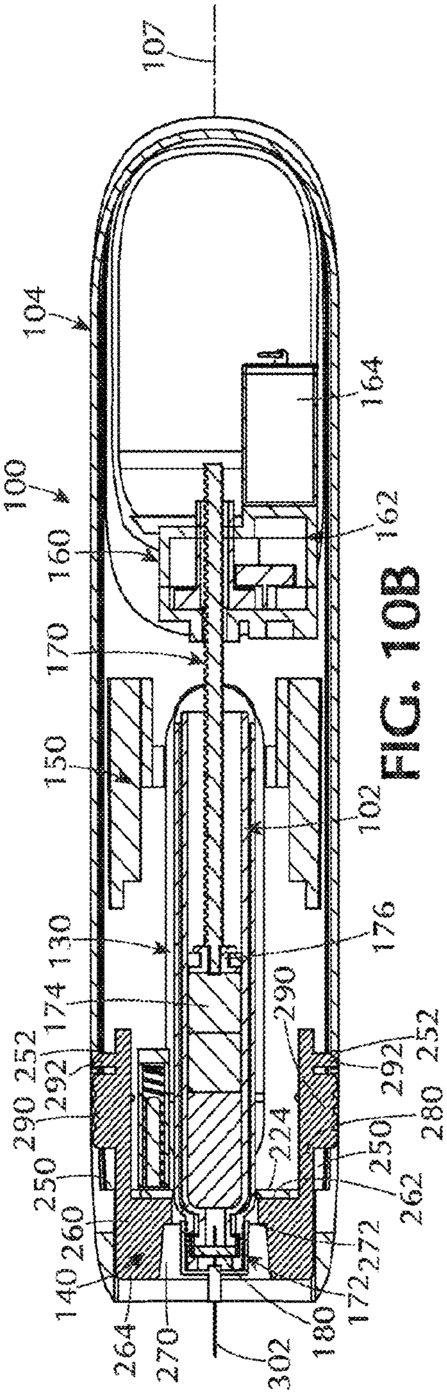
Figure 10C:
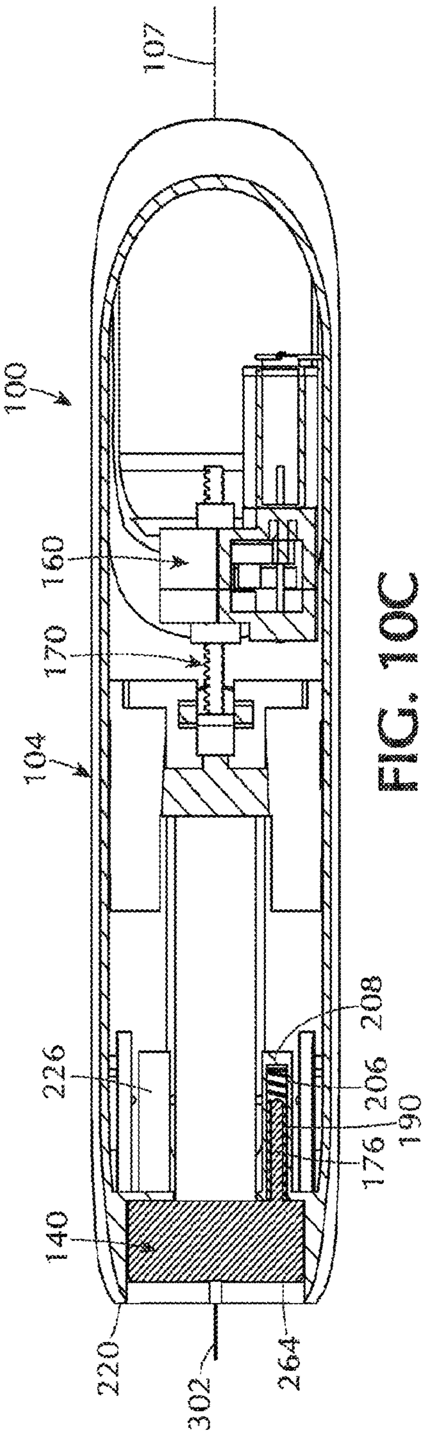

Reference is now made to FIGS. 10A, 10B and 10C, which are simplified respective pictorial and two section view illustrations of the injector 100 of FIGS. 1-3 operated by a user, in a needle exposure operative orientation, section views being taken along lines B-B and C-C respectively in FIG. 10A.

The injector 100 is seen in needle exposure operative orientation in FIGS. 10A-10C, following removal of the outer needle cap 306 along with the internal needle cap 304 from needle 302.

It is seen particularly in FIG. 9B that the needle 302 with the needle hub remain threadably attached to the externally threaded end 172 of the cartridge enclosure assembly 130.

It is seen in FIGS. 10A-10C that the needle hiding element 140 remains disposed within the enclosure formed by the housing portions 104 and 106, such that the forwardly facing surface 264 of the needle hiding element 140 is rearwardly spaced from the forward ends 200 and 220 of housing portions 106 and 104 respectively.

In this needle exposure operative orientation, the needle 302 is exposed and the needle hiding element 140 is disposed in a retracted locked orientation, which is the rearwardmost position of the needle hiding element 140. It is specifically seen in FIG. 10B that in this retracted locked orientation of the needle hiding element 140, the snap protrusions 252 remain inserted into snap cut-outs 292 of the bottom housing portion 104 and the buttons 290 are positioned adjacent the rearward ends of the cut-outs 250. The needle hiding element 140 is temporarily locked in its retracted position and is restrained from forward longitudinal displacement along longitudinal axis 107 by means of engagement between snap protrusions 292 with snap cut-outs 252.

It is also seen particularly in FIG. 10C that the biasing springs 190 remain disposed in a compressed operative orientation, but are prevent from displacing the needle hiding element 140 forwardly due to the locking engagement of the snap protrusions 292 with the snap cut-outs 252.

It is particularly seen in FIG. 10B that buttons 290 of the needle hiding element 140 remain rearwardly spaced from the forward ends of cut-outs 250 of the bottom housing portion 104.

It is also seen in FIG. 10B that the medicament is confined within the medicament cartridge 102 by means of the piston 174 and the piston contact element 176 of the plunger rod 170 engages the piston 174. The needle 302 penetrates the septum 180 of the medicament cartridge 102 and thus is disposed in fluid communication with the medicament confined within the medicament cartridge 102.

Figure 11A:
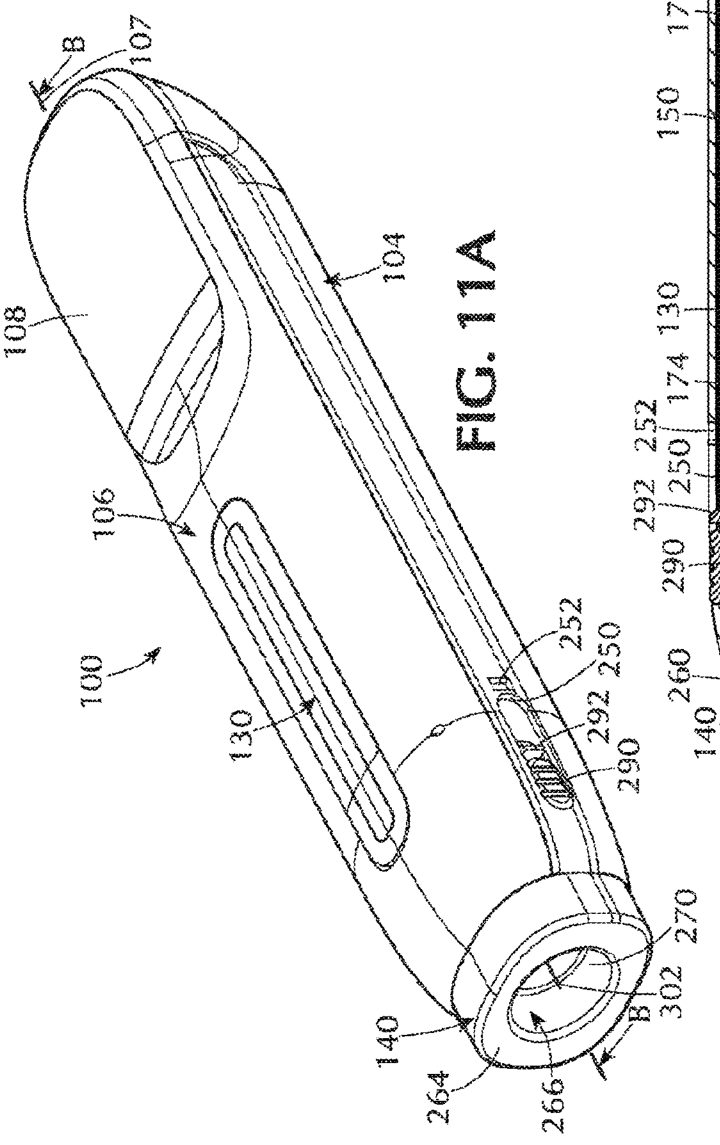
FIGS. 11A and 11B are simplified respective pictorial and section view illustrations of the injector of FIGS. 1-3 operated by a user, in a needle hiding operative orientation, section view being taken along lines B-B in FIG. 11A.
Figure 11B:
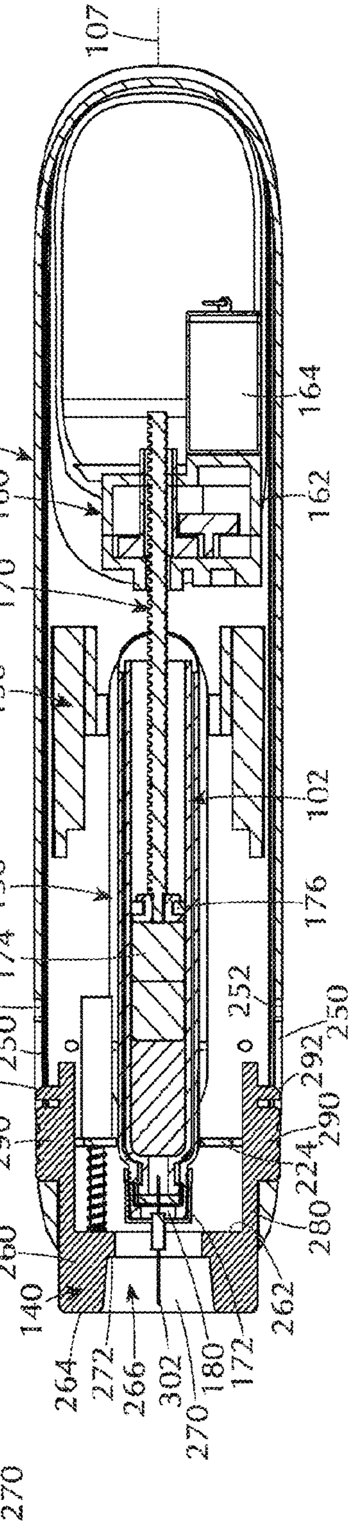

Reference is now made to FIGS. 11A and 11B, which are simplified respective pictorial and section view illustrations of the injector 100 of FIGS. 1-3 operated by a user, in a needle hiding operative orientation, section view being taken along lines B-B in FIG. 11A.

The injector 100 is seen in needle hiding operative orientation in FIGS. 11A & 11B, following pressing the buttons 290 of the needle hiding element 140 by the user, and thus unlocking the needle hiding element 140 from the housing portions 104 and 106 and causing forward longitudinal displacement of the needle hiding element 140 relative to the housing portions 104 and 106 under the biasing force of springs 190. The snap protrusions 292 of the flexible arms 280 and the corresponding features of the housing 104, 106, namely the snap cut-outs 252, are thus designed to provide the locked retracted orientation of the needle hiding element 140. That locked position can be unlocked by the user by simultaneously pressing on the buttons 290, whereby the snap protrusions 292 are disengaged from the corresponding snap cut-outs 252.

It is seen in FIGS. 11A & 11B that upon inwardly pressing the buttons 290 by the user, the needle hiding element 140 is unlocked from the housing portions 104 and 106 by temporarily inwardly deflecting mounting arms 280 of the needle hiding element 140, causing snap protrusions 252 of the needle hiding element 140 to be released from snap cut-outs 252 of the bottom housing portion 104, thus in turn causing forward axial slidable displacement of the needle hiding element 140 relative to the housing portions 104 and 106 under the urge of biasing springs 190.

It is particularly seen in FIGS. 11A & 11B that the buttons 290 of the needle hiding element 140 are supported against the forward ends of the cut-outs 250 of the bottom housing portion 104, and thus the needle hiding element 140 is restrained from further forward displacement along longitudinal axis 107 relative to the housing portions 104 and 106 and removal therefrom.

It is seen that in this needle hiding operative orientation that the biasing springs 190 are disposed in their non-stressed operative orientation, thus biasing the needle hiding element 140 to an extended position, which is the forwardmost position of the needle hiding element 140, in which the needle hiding element 140 extends forwardly from the forward end 200 and 220 of the upper and bottom housing portions respectively, such that the forwardly facing surface 264 of the needle hiding element 140 is forwardly spaced from the forward ends 200 and 220 and the needle 302 is hidden within the opening 266 of the needle hiding element 140 and thus hidden from view of the user.

It is particularly seen that the buttons 290 of the needle hiding element 140 are disposed at the forward end of the cut-outs 250 of the bottom housing portion 104 and the snap protrusions 292 are forwardly spaced from the snap cut-outs 252 in the bottom housing portion 104 in this needle hiding operative orientation.

It is also seen in FIG. 11B that the medicament is confined within the medicament cartridge 102 by means of the piston 174 and the piston contact element 176 of the plunger rod 170 engages the piston 174. The drive assembly 160 that drives the plunger rod 170 along the longitudinal axis 107 is preferably similar in all respects to the one described in PCT patent application PCT/IL2017/050607, which is incorporated by reference herein in its entirety.

It is also seen in FIG. 11B that the needle 302 penetrates the septum 180 of the medicament cartridge 102 and thus remains disposed in fluid communication with the medicament confined within the medicament cartridge 102.

Figure 12A:
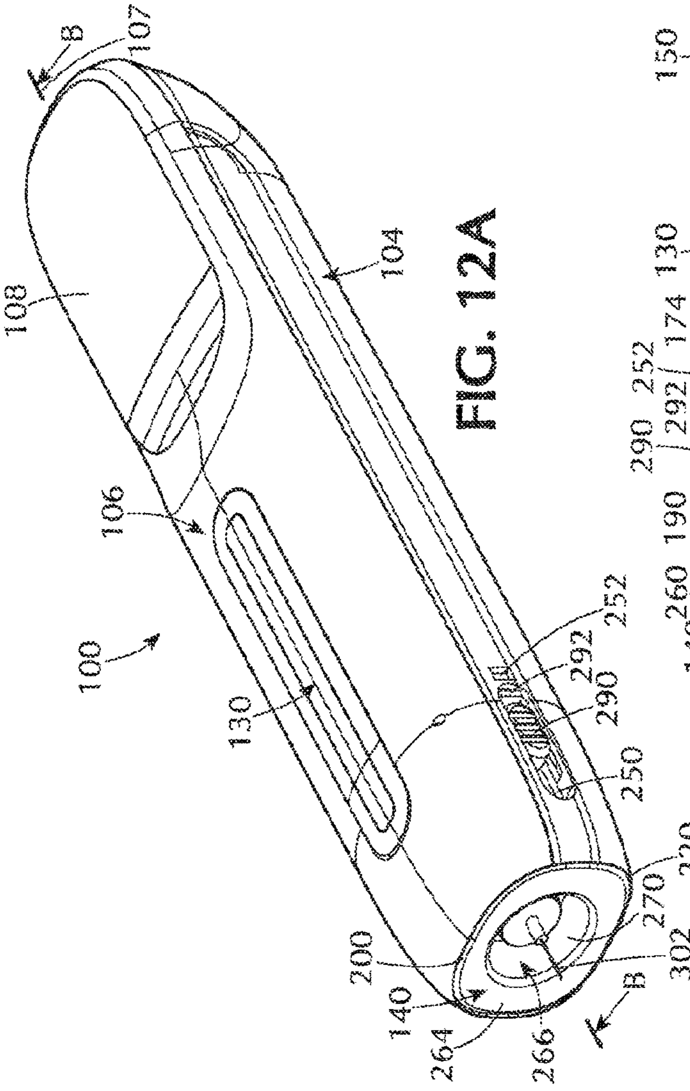
FIGS. 12A and 12B are simplified respective pictorial and section view illustrations of the injector of FIGS. 1-3 operated by a user, in an injection operative orientation, section view being taken along lines B-B in FIG. 12A.
Figure 12B:
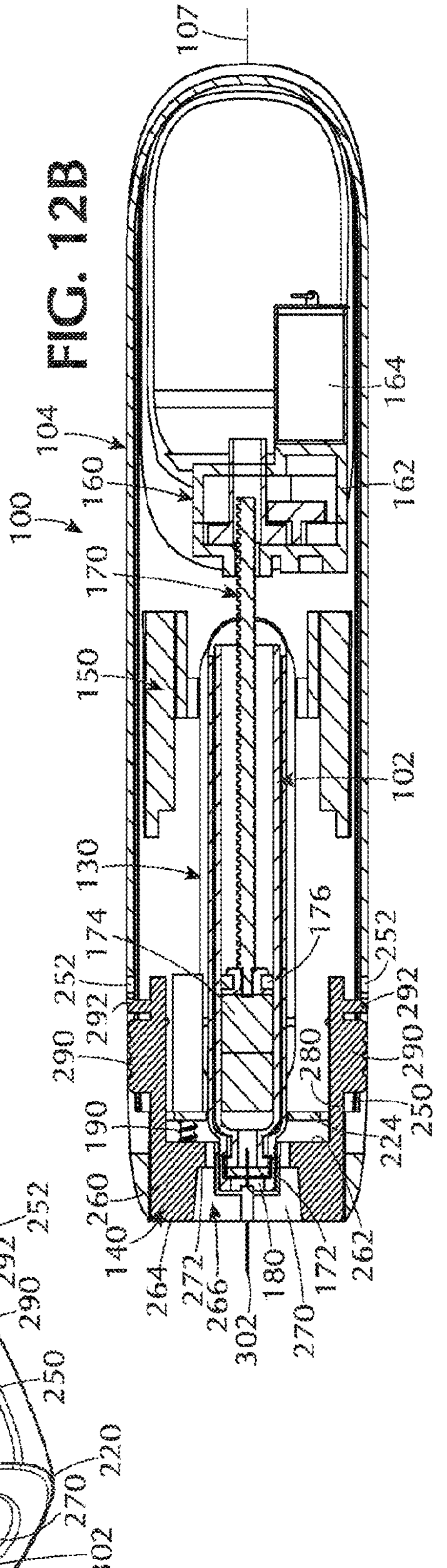

Reference is now made to FIGS. 12A and 12B, which are simplified respective pictorial and section view illustrations of the injector 100 of FIGS. 1-3 operated by a user, in an injection operative orientation, section view being taken along lines B-B in FIG. 12A.

The injector 100 is seen in injection operative orientation in FIGS. 12A & 12B, following pressing of the injector 100 against an injection site on the skin of the user. Upon pressing the injector 100 against the injection site, the forwardly facing surface 264 of the needle hiding element 140 engages the skin and as the user proceeds pushing the injector 100 axially forwardly against the skin, the needle hiding element 140 is slidably rearwardly displaced against the urge of the biasing springs 190.

It is a particular feature of an embodiment of the present invention that is this injection operative orientation, the needle hiding element 140 is rearwardly displaced until the forwardly facing surface 264 thereof is generally aligned with the forward ends 200 and 220 of the housing portions 106 and 104 respectively. In this injection operative orientation, the needle hiding element 140 is disposed in a partially retracted orientation, in which the needle hiding element 140 is positioned in an intermediate position, which is disposed forwardly of its retracted position and rearwardly of its extended position.

It is a further particular feature of an embodiment of the present invention that the needle hiding element 140 is not locked in this partially retracted orientation and thus enabled to be slidably biased forwardly relative to the housing portions 104 and 106 upon removal of pressure that is applied thereon by the user.

It is seen in FIGS. 12A & 12B that the buttons 290 of the needle hiding element 140 in its partially retracted orientation are slightly spaced from the forward ends of the cut-outs 250 of the bottom housing portion 104, but they are rearwardly spaced to a lesser extent in comparison to FIG. 10B. The snap protrusions 292 are disposed within cut-outs 250 and are forwardly spaced from snap cut-outs 252 of the bottom housing portion 104, thus the needle hiding element 140 is not locked with respect to the housing portions 104 and 106.

It is seen in this injection operative orientation that the biasing springs 190 are disposed in their partially-compressed operative orientation. The needle 302 in this injection operative orientation extends forwardly from the needle hiding element 140 and the housing portions 104 and 106, thus penetrates the skin of the user.

It is also seen in FIG. 12B that the medicament is ejected from the medicament cartridge 102 via needle 302 by means of the drive assembly 160, which advances the plunger rod 170 axially forwardly and effects displacement of the piston 174 relative to the medicament cartridge 102. The drive assembly 160 that drives the plunger rod 170 along the longitudinal axis 107 is preferably similar in all respects to the one described in PCT patent application PCT/IL2017/050607, which is incorporated by reference herein in its entirety.

Figure 13A:
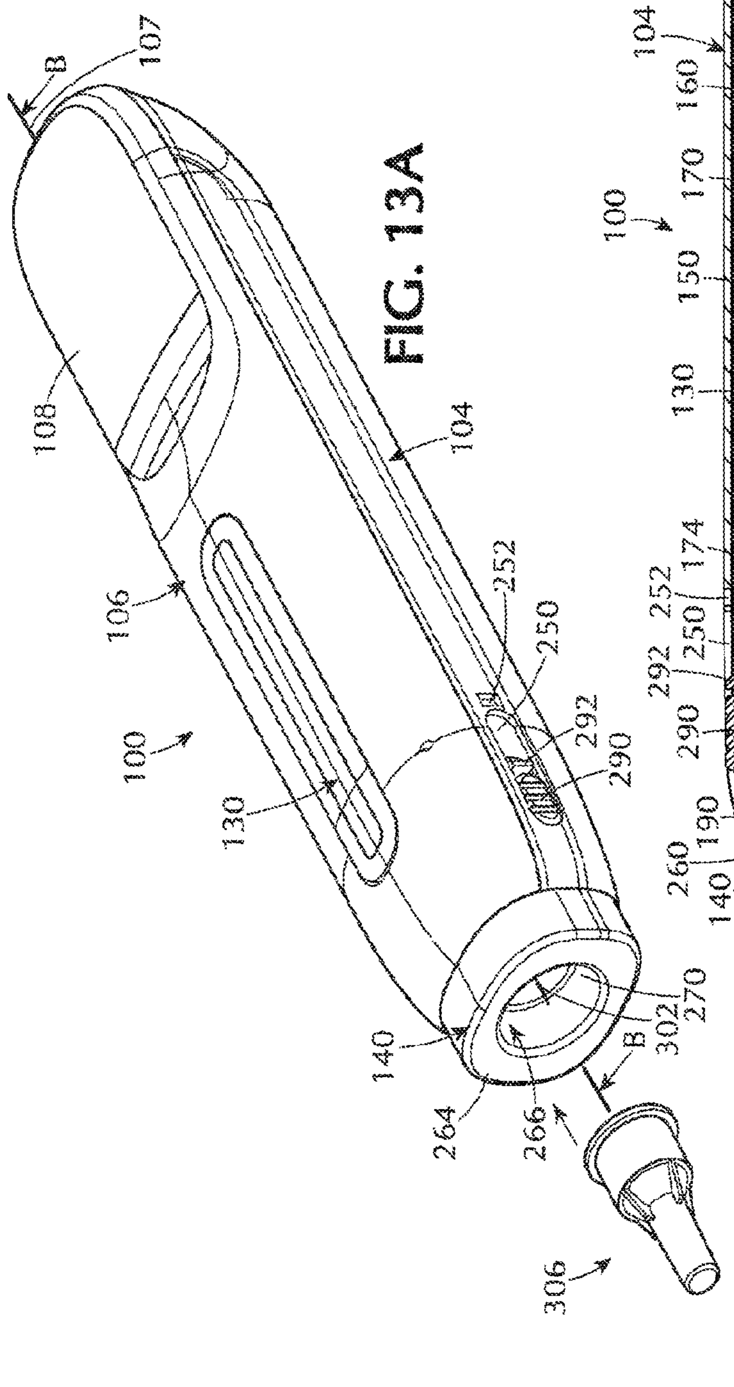
FIGS. 13A and 13B are simplified respective pictorial and section view illustrations of the injector of FIGS. 1-3 operated by a user, in a needle cover attachment operative orientation, section view being taken along lines B-B in FIG. 13A.
Figure 13B:
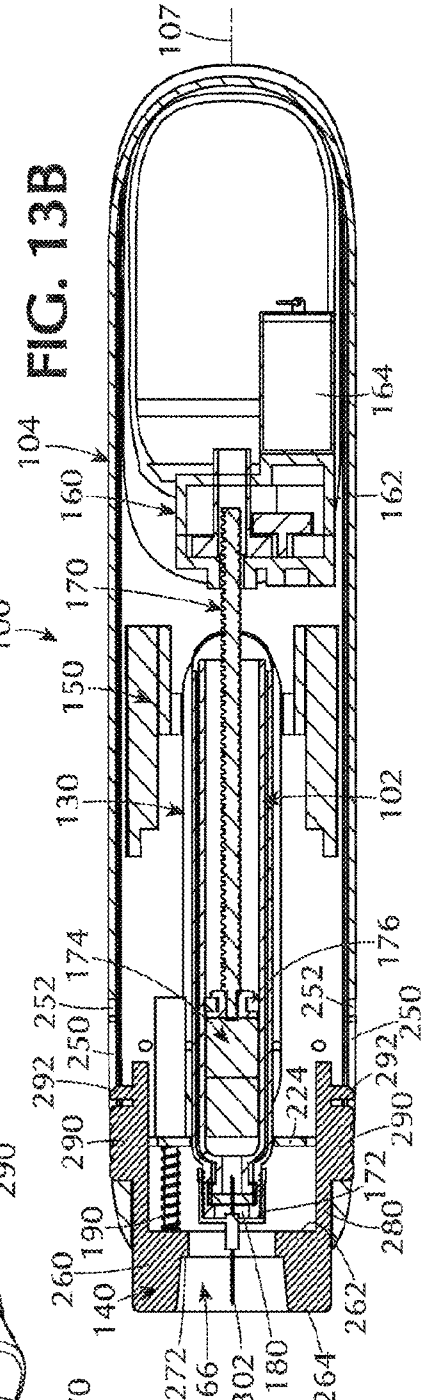

Reference is now made to FIGS. 13A and 13B, which are simplified respective pictorial and section view illustrations of the injector 100 of FIGS. 1-3 operated by a user, in a needle cover attachment operative orientation, section view being taken along lines B-B in FIG. 13A.

The injector 100 is seen just prior to attachment of the outer needle cap 306 to the needle 302 in FIGS. 13A & 13B, following release of the injector 100 from the skin of the user.

Upon release of the injector 100 from the skin, the needle hiding element 140 is biased to be displaced forwardly relative to the housing portions 104 and 106 to its extended orientation under the urge of biasing springs 190.

It is particularly seen in FIGS. 13A & 13B that upon release of the injector 100 from the skin, the needle hiding element 140 is disposed in the same orientation as described with reference to FIGS. 11A & 11B. Specifically, the buttons 290 of the needle hiding element 140 are supported against the forward ends of the cut-outs 250 of the bottom housing portion 104, and thus the needle hiding element 140 is restrained from further forward displacement along longitudinal axis 107 relative to the housing portions 104 and 106 and removal therefrom.

It is seen that in this operative orientation the biasing springs 190 are disposed in their non-stressed operative orientation, thus biasing the needle hiding element 140 to an extended position, which is the forwardmost position of the needle hiding element 140, in which the needle hiding element 140 extends forwardly from the forward end 200 and 220 of the upper and bottom housing portions respectively, such that the forwardly facing surface 264 of the needle hiding element 140 is forwardly spaced from the forward ends 200 and 220 and the needle 302 is hidden within the opening 266 of the needle hiding element 140 and thus hidden from view of the user.

It is particularly seen that the buttons 290 of the needle hiding element 140 are disposed at the forward end of the cut-outs 250 of the bottom housing portion 104 and the snap protrusions 292 are forwardly spaced from the snap cut-outs 252 in the bottom housing portion 104 in this operative orientation.

It is also seen in FIG. 13B that the medicament cartridge 102 is empty. Alternatively, a certain dosage of the medicament could have been injected rather than the full amount of medicament contained in the medicament cartridge 102.

Figure 14A:
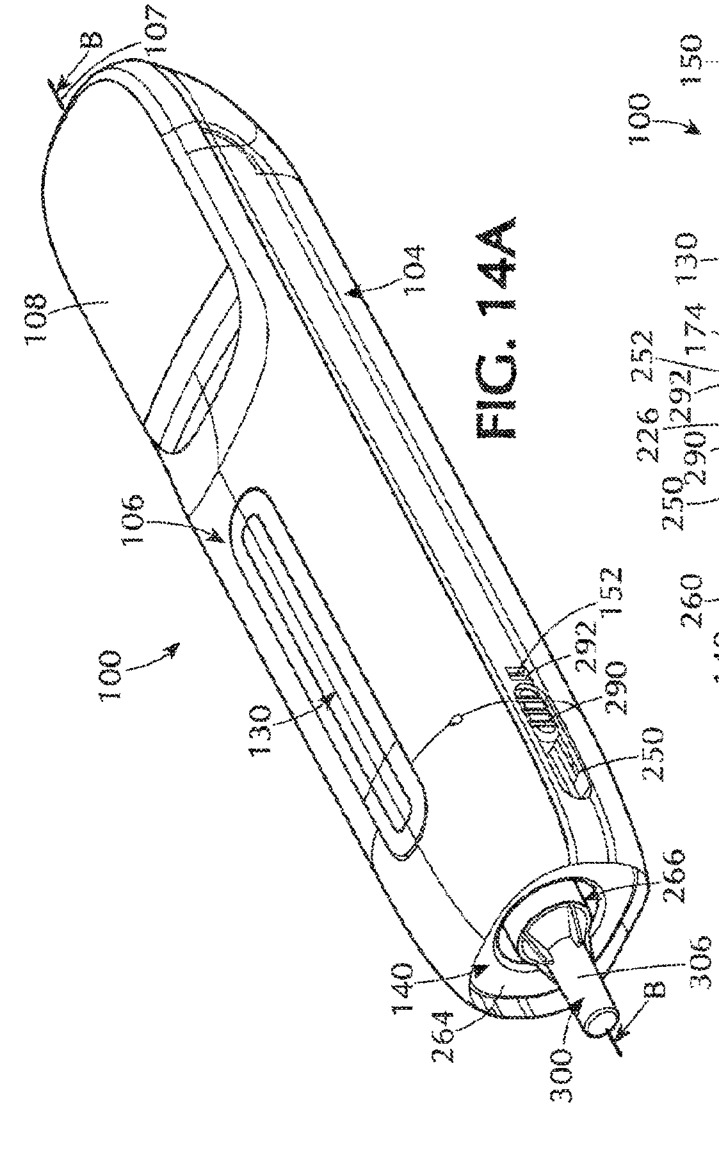
FIGS. 14A and 14B are simplified respective pictorial and section view illustrations of the injector of FIGS. 1-3 operated by a user, in a needle cover attached operative orientation, section view being taken along lines B-B in FIG. 14A.
Figure 14B:
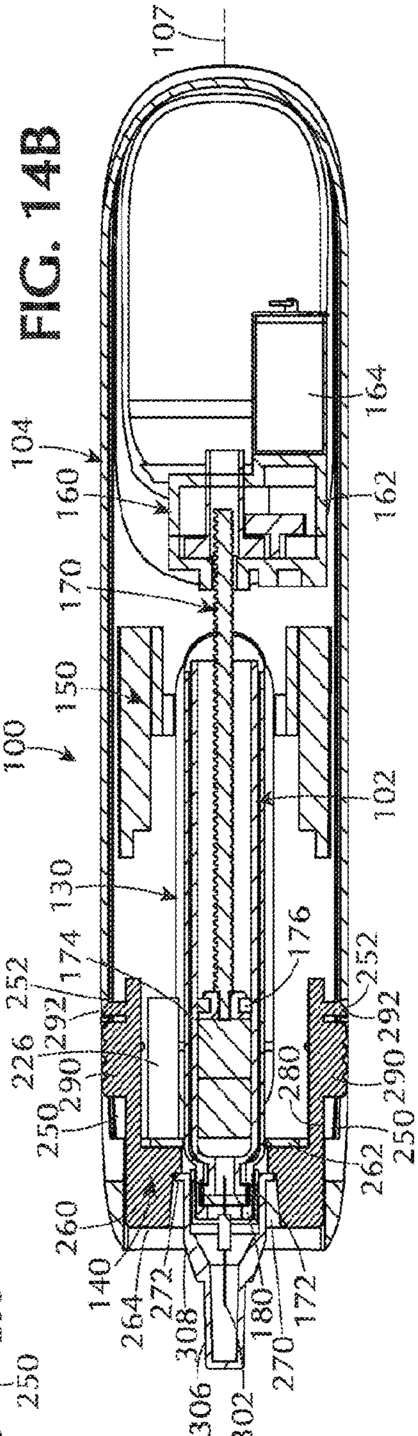

Reference is now made to FIGS. 14A and 14B, which are simplified respective pictorial and section view illustrations of the injector 100 of FIGS. 1-3 operated by a user, in a needle cover attached operative orientation, section view being taken along lines B-B in FIG. 14A.

The injector 100 is seen in needle cover attached operative orientation in FIGS. 14A & 14B, following attachment of the outer needle cap 306 to the needle 302. This operative orientation is essentially similar to the operative orientation illustrated and described with reference to FIGS. 9A-9C, besides that a portion or all of the medicament is ejected from the medicament cartridge 102 in this operative orientation.

Preferably, the outer needle cap 306 is now mounted over the needle 302 and the needle hub.

It is seen particularly in FIGS. 14A & 14B that upon attachment of the outer needle cap 308 to the injector 100, the circumferential rear end 308 of the outer needle cap 308 engages the forwardly facing shoulder 272 of the needle hiding element 140. Engagement of the outer needle cap 308 with the needle hiding element 140 causes rearward slidable displacement of the needle hiding element 140 relative to the housing portions 104 and 106 against the urge of the biasing springs 190.

It is seen in FIGS. 14A & 14B that the needle hiding element 140 is now disposed within the enclosure formed by the housing portions 104 and 106, such that the forwardly facing surface 264 of the needle hiding element 140 is rearwardly spaced from the forward ends 200 and 220 of housing portions 106 and 104 respectively.

It is a particular feature of an embodiment of the present invention that the needle 302 in this needle attached operative orientation is covered by the outer needle cap 306 and the needle hiding element 140 is disposed in a retracted locked orientation, which is the rearwardmost position of the needle hiding element 140. It is specifically seen that in this retracted locked orientation of the needle hiding element 140, the snap protrusions 252 are rearwardly displaced relative to the housing portions 104 and 106 and are now inserted into snap cut-outs 292 of the bottom housing portion 104 and the buttons 290 are positioned adjacent the rearward ends of the cut-outs 250. The needle hiding element 140 is temporarily locked in its retracted position and is restrained from forward longitudinal displacement along longitudinal axis 107 by means of engagement between snap protrusions 292 with snap cut-outs 252. The locking of the snap protrusions 292 with snap cut-outs 252 is enabled due to temporary inward deflection of the mounting arms 280 of the needle hiding element 140.

It is also noted that the biasing springs 190 are now disposed in their compressed operative orientation, but are prevented from displacing the needle hiding element 140 forwardly due to the locking engagement of the snap protrusions 292 with the snap cut-outs 252.

It is particularly seen that buttons 290 of the needle hiding element 140 are rearwardly spaced from the forward end of cut-outs 250 of the bottom housing portion 104.

It is appreciated that if medicament still remains within the medicament container 102 and the user wishes to perform injection of an additional dose of medication while hiding the needle 302 during needle penetration into the skin and needle retraction from the skin, the user has to press buttons 290 of the needle hiding element 140 inwardly towards the longitudinal axis 107 in order to unlock the needle hiding element 140 from the housing portions 104 and 106.

It is a particular feature of an embodiment of the present invention that the injector 100 includes a needle hiding element 140 that is displaceable relative to the housing portions 104 and 106 of the injector 100 and positionable in an extended orientation exposing the needle, a retracted orientation, in which the needle hiding element 140 is locked relative to the housing portions 104 and 106 and in a partially retracted orientation during injection of the medicament from the medicament cartridge 102.

It is appreciated that alternatively, instead of the illustrated two mounting arms 280 of the needle hiding element 140, any other number or configuration of such mounting arms of the needle hiding element 140 which enables locking/unlocking of the needle hiding element 140 from the housing portions 104 and 106 in certain operative orientations is considered to be within the scope of embodiments of the present invention. For example, a single mounting arm 280 which engages a cut-out formed on the back wall 240 of the bottom housing portion 104, rather than on the side walls 242 thereof may be employed as part of the present invention.

It is noted that alternative medicament cartridge insertion methods into the injector 100 are considered to be within the scope of the present invention, such as for example providing an opening at the forward end of the housing of the injector 100 and rotatably inserting the medicament cartridge 102 therethrough. Other methods of medicament cartridge insertion into the injector 100 are also considered to be within the scope of the present invention.

It will be appreciated by persons skilled in the art that the present invention is not limited by what has been particularly shown and described hereinabove. Rather the present invention includes both combinations and subcombinations of various features described herein and improvements and variations which would occur to persons skilled in the art upon reading the foregoing description and which are not in the prior art.

The invention claimed is:

1. An injector comprising:

a housing arranged along a longitudinal axis and configured to receive a medicament cartridge;

an injection drive mechanism for driving a piston, said piston forming a part of said medicament cartridge, said injection drive mechanism injecting a medicament when said piston is forwardly displaced; and a needle hiding element that hides and prevents access to a needle tip, which is slidably attached to said housing and positionable in at least one of an extended orientation and a retracted orientation, wherein in said extended orientation said needle hiding element protrudes forwardly from said housing and in said retracted orientation, said needle hiding element is locked relative to said housing;

wherein the needle hiding element includes at least a flexible arm, extending axially and comprising a snap-fit locking feature that can be engaged in a corresponding feature provided on the housing and a radially protruding button that can be handled by a user for deflecting the arm and axially moving the needle hiding element, whereby the user can position the needle hiding element in one of said extended and retracted orientations, wherein the radially protruding button can be engaged by a longitudinal cut-out formed on a sidewall of the housing adjacent to the corresponding feature.

2. The injector according to claim 1, wherein in said extended orientation said needle hiding element is slidable relative to said housing and in said retracted orientation the needle hiding element does not protrude forwardly from said housing or protrudes to a lesser extent than in said extended orientation.

3. The injector according to claim 1, wherein said needle hiding element is also positionable in a partially retracted orientation, in which said needle hiding element protrudes forwardly from said housing to a greater extent than in said retracted orientation and is slidably moveable relative to said housing.

4. The injector according to claim 1, wherein said needle hiding element is biased to be displaced forwardly under an urge of at least one biasing element, which is supported between said housing and said needle hiding element.

5. The injector according to claim 1, wherein the snap-fit locking feature of the flexible arm and the corresponding feature of the housing are designed to provide the locked retracted orientation of the needle hiding element, that can be unlocked by the user by pressing on the button whereby the locking feature of the arm is disengaged from the corresponding feature of the housing.

6. The injector according to claim 5, wherein the needle hiding element includes a pair of opposing flexible arms, each provided with a snap-fit locking feature and a button, whereby the locked retracted orientation of the needle hiding element can be unlocked by the user by simultaneously pressing on the buttons for simultaneous deflection of the arms.

7. An injector comprising:
- a housing arranged along a longitudinal axis and configured to receive a medicament cartridge;
- an injection drive mechanism for driving a piston, said injection drive mechanism injecting a medicament when said piston is forwardly displaced; and
- a needle hiding element that hides and prevents access to a needle tip, which is slidably attached to said housing and positionable in at least one of an extended orientation and a retracted orientation, wherein in said extended orientation said needle hiding element protrudes forwardly from said housing and in said retracted orientation, said needle hiding element is locked relative to said housing;
- wherein the needle hiding element includes at least a flexible arm, extending axially and comprising a snap-fit locking feature that can be engaged in a corresponding feature provided on the housing and a radially protruding button that can be handled by a user for deflecting the arm and axially moving the needle hiding element, whereby the user can position the needle hiding element in one of said extended and retracted orientations, wherein the radially protruding button can be engaged by a longitudinal cut-out formed on a sidewall of the housing adjacent to the corresponding feature.

8. The injector according to claim 7, wherein in said extended orientation said needle hiding element is slidable relative to said housing and in said retracted orientation the needle hiding element does not protrude forwardly from said housing or protrudes to a lesser extent than in said extended orientation.

9. The injector according to claim 7, wherein said needle hiding element is also positionable in a partially retracted orientation, in which said needle hiding element protrudes forwardly from said housing to a greater extent than in said retracted orientation and is slidably moveable relative to said housing.

10. The injector according to claim 7, wherein said needle hiding element is biased to be displaced forwardly under an urge of at least one biasing element, which is supported between said housing and said needle hiding element.

11. The injector according to claim 7, wherein the snap-fit locking feature of the flexible arm and the corresponding feature of the housing are designed to provide the locked retracted orientation of the needle hiding element, that can be unlocked by the user by pressing on the button whereby the locking feature of the arm is disengaged from the corresponding feature of the housing.

12. The injector according to claim 11, wherein the needle hiding element includes a pair of opposing flexible arms, each provided with a snap-fit locking feature and a button, whereby the locked retracted orientation of the needle hiding element can be unlocked by the user by simultaneously pressing on the buttons for simultaneous deflection of the arms.

13. A method of using a medicament injector, the method comprising:
- inserting a medicament cartridge into a housing of an injector, the housing being arranged along a longitudinal axis;
- retracting a needle hiding element of said injector that hides and prevents access to a needle tip and locking said needle hiding element relative to said housing in a retracted orientation;
- attaching a needle to said medicament cartridge;
- releasing said needle hiding element such that said needle hiding element is returned to an extended orientation protruding forwardly from said using;
- pressing said injector against an injection site; and
- driving, by an injection drive mechanism of said injector, a piston that forms a part of said medicament cartridge, said injection drive mechanism injecting a medicament via said needle when said piston is forwardly displaced;
- wherein the needle hiding element includes at least a flexible arm, extending axially and comprising a snap-fit locking feature that can be engaged in a corresponding feature provided on the housing and a radially protruding button for deflecting the arm and axially moving the needle hiding element, wherein the radially protruding button can be engaged by a longitudinal cut-out formed on a sidewall of the housing adjacent to the corresponding feature.

14. The method according to claim 13, wherein in said extended orientation said needle hiding element is slidable relative to said housing and in said retracted orientation the needle hiding element does not protrude forwardly from said housing or protrudes to a lesser extent than in said extended orientation.

15. The method according to claim 13, further comprising:
- positioning said needle hiding element in a partially retracted orientation, in which said needle hiding element protrudes forwardly from said housing to a greater extent than in said retracted orientation and is slidably moveable relative to said housing.

16. The method according to claim 13, wherein said needle hiding element is biased to be displaced forwardly under an urge of at least one biasing element, which is supported between said housing and said needle hiding element.

17. The method according to claim 13, wherein the snap-fit locking feature of the flexible arm and the corresponding feature of the housing are designed to provide the locked retracted orientation of the needle hiding element, said method further comprising:

unlocking the snap-fit locking feature by pressing on the button to disengage the locking feature of the arm from the corresponding feature of the housing.

* * * * *